US012202888B2

United States Patent
Achkar et al.

(10) Patent No.: US 12,202,888 B2
(45) Date of Patent: Jan. 21, 2025

(54) **HIGH-AFFINITY *MYCOBACTERIUM TUBERCULOSIS* CAPSULE-SPECIFIC HUMAN MONOCLONAL ANTIBODY**

(71) Applicant: Albert Einstein College of Medicine, Bronx, NY (US)

(72) Inventors: Jacqueline M. Achkar, Brooklyn, NY (US); Jonathan Lai, Dobbs Ferry, NY (US); Elise Ishida, Aiea, HI (US); Daniel Hofmann, Moembris (DE); Tingting Chen, Bronx, NY (US)

(73) Assignee: Albert Einstein College of Medicine, Bronx, NY (US)

( * ) Notice: Subject to any disclaimer, the term of this patent is extended or adjusted under 35 U.S.C. 154(b) by 0 days.

(21) Appl. No.: 18/309,590

(22) Filed: Apr. 28, 2023

(65) Prior Publication Data

US 2023/0365663 A1    Nov. 16, 2023

Related U.S. Application Data

(60) Division of application No. 17/247,532, filed on Dec. 15, 2020, now Pat. No. 11,643,455, which is a
(Continued)

(51) Int. Cl.
*C07K 16/12* (2006.01)
*G01N 33/53* (2006.01)
(Continued)

(52) U.S. Cl.
CPC ..... *C07K 16/1289* (2013.01); *G01N 33/5302* (2013.01); *G01N 33/54388* (2021.08); *G01N 33/5695* (2013.01); *A61K 2039/505* (2013.01); *C07K 2317/56* (2013.01); *C07K 2317/565* (2013.01)

(58) Field of Classification Search
CPC ............ C07K 16/1289; C07K 2317/56; C07K 2317/565; G01N 33/5695; G01N 33/5302; G01N 33/54388; G01N 33/558
See application file for complete search history.

(56) References Cited

U.S. PATENT DOCUMENTS

| | | | |
|---|---|---|---|
| 6,194,222 B1 * | 2/2001 | Buechler | G01N 35/00693 436/805 |
| 2002/0034763 A1 | 3/2002 | Glatman-Freedman et al. | |
| 2016/0083458 A1 | 3/2016 | Katsuragi et al. | |
| 2016/0312314 A1 | 10/2016 | Storch et al. | |
| 2017/0002064 A1 | 1/2017 | Monson | |

FOREIGN PATENT DOCUMENTS

| | | | | |
|---|---|---|---|---|
| WO | WO-2019200255 A1 * | 10/2019 | ............ | A61P 31/06 |
| WO | 2020/089380 A1 | 5/2020 | | |
| WO | 2020/160560 A2 | 8/2020 | | |

OTHER PUBLICATIONS

Moser et al. "Clinical applications of capillary electrophoresis based immunoassays", 2014, Electrophoresis, vol. 35, p. 937-955. (Year: 2014).*
Singhal et al. "Microfluidic Measurement of Antibody-Antigen Binding Kinetics from Low-Abundance Samples and Single Cells", Oct. 15, 2010, Analytical Chemistry, vol. 82, No. 20, p. 8671-8679. (Year: 2010).*

(Continued)

*Primary Examiner* — Gary B Nickol
*Assistant Examiner* — Amelia Nicole Dickens
(74) *Attorney, Agent, or Firm* — Fox Rothschild LLP

(57) ABSTRACT

Provided are high affinity *Mycobacterium tuberculosis* capsule-specific antibodies and fragments thereof, as well as methods of use and devices employing such antibodies and/or fragments.

19 Claims, 9 Drawing Sheets
Specification includes a Sequence Listing.

Related U.S. Application Data continuation-in-part of application No. 17/047,256, filed as application No. PCT/US2019/027218 on Apr. 12, 2019, now abandoned.

(60) Provisional application No. 62/739,428, filed on Oct. 1, 2018, provisional application No. 62/657,253, filed on Apr. 13, 2018.

(51) Int. Cl.
*G01N 33/543* (2006.01)
*G01N 33/569* (2006.01)
*A61K 39/00* (2006.01)

(56) References Cited

OTHER PUBLICATIONS

International Search Report and Written Opinion mailed Apr. 18, 2022, in International Application No. PCT/US2021/063461, 19 pages.

Navoa et al., "Specificity and Diversity of Antibodies to *Mycobacterium tuberculosis* Arabinomannan", Jan. 2003, Clinical and Diagnostic Laboratory Immunology, vol. 10 No. 1, p. 88-94. (Year: 2003).

Tully et al., Hypothetical Protein CMB92_01875, Partial [Flammeovirgaceae bacterium], Genbank Entry, Sep. 11, 2017 [retrieved on Aug. 6, 2019], Retrieved from the Internet: <URL:https://www.ncbi.nlm.nih.gov/protein/MBE49488>; pp. 1-2.

* cited by examiner

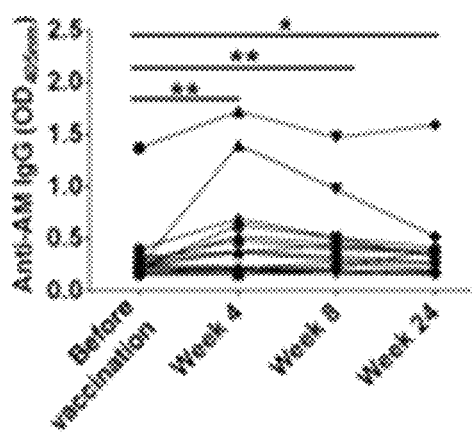
Fig. 1A IgG primary vaccination
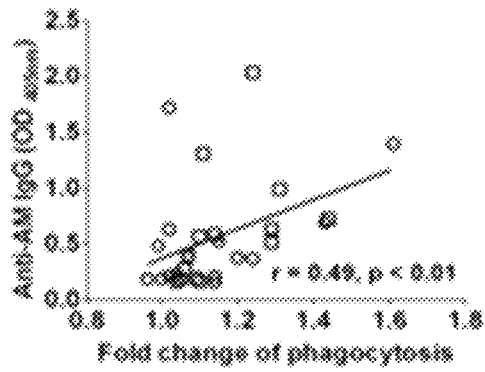
Fig. 1B
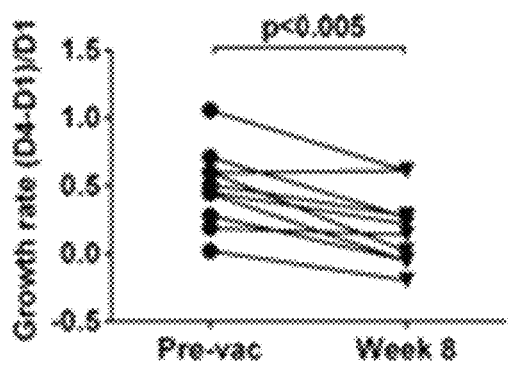
Fig. 1C
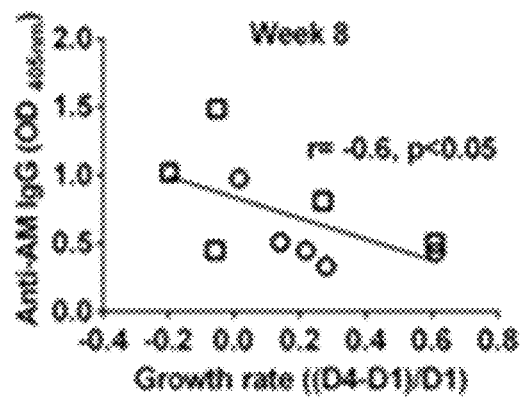
Fig. 1D
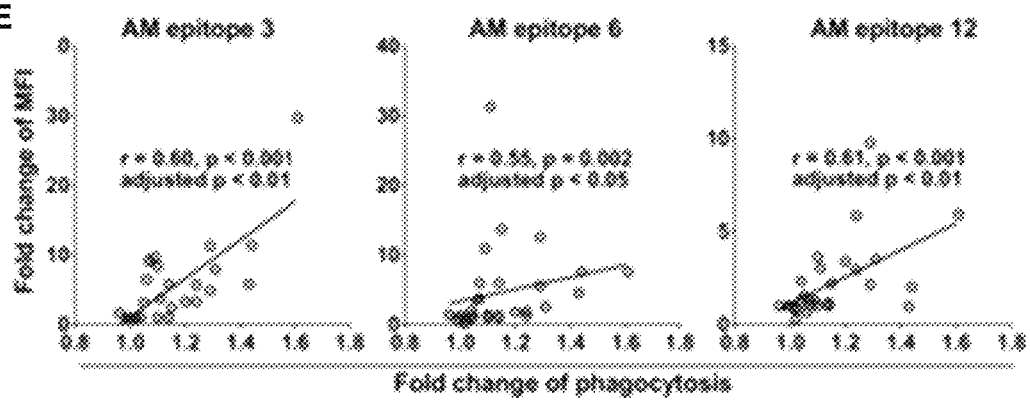
Fig. 1E

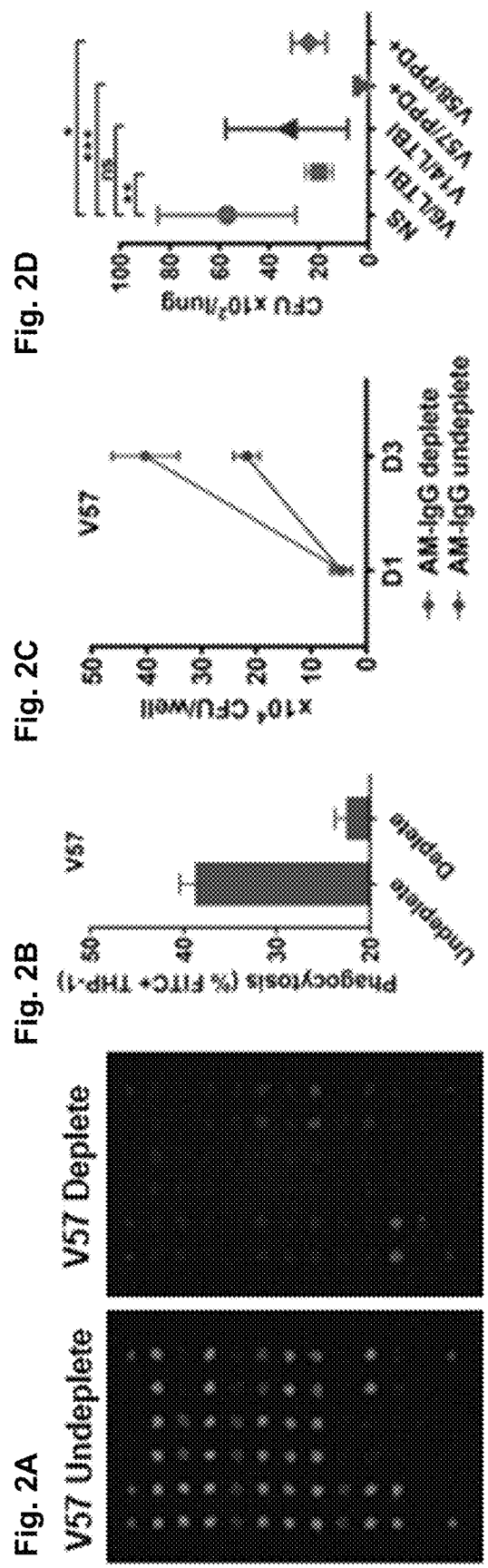

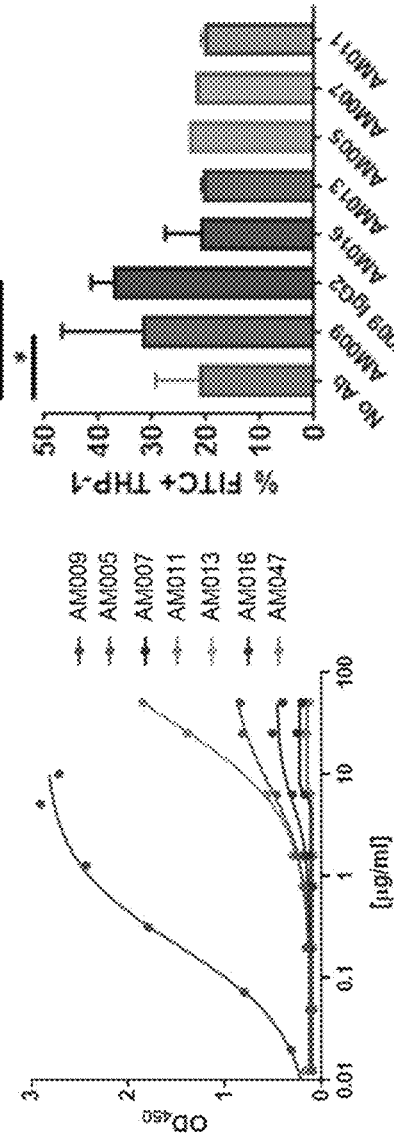
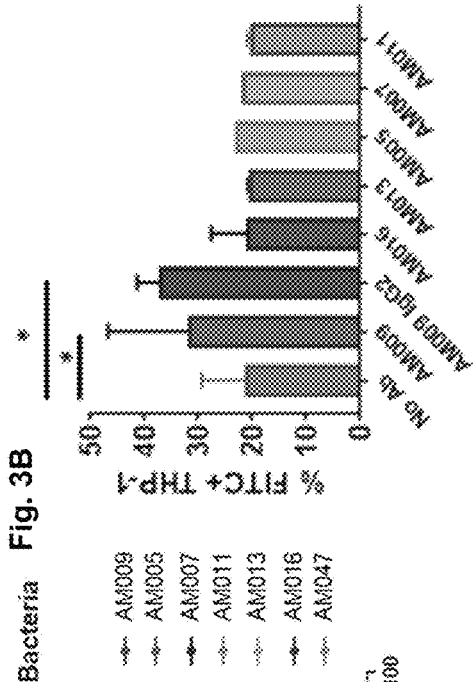
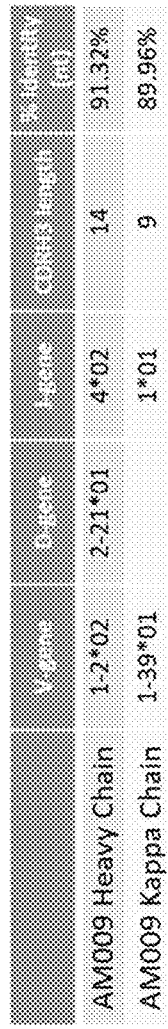
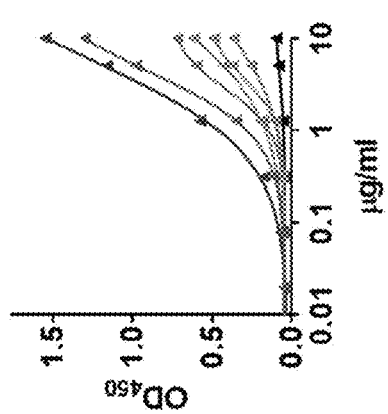
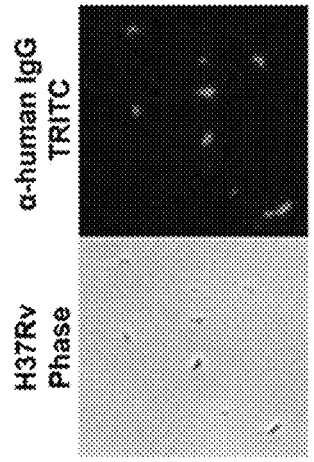

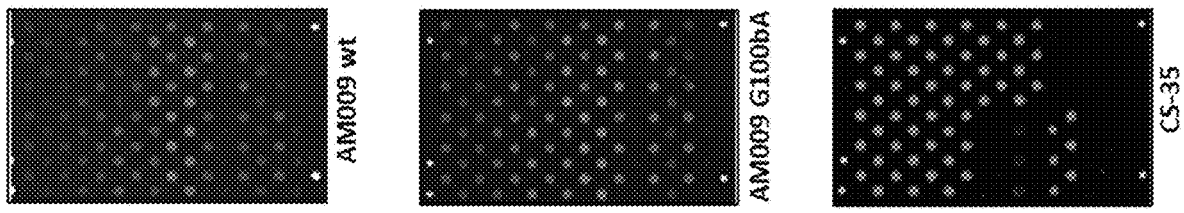
Fig. 4D
Fig. 4A
AM009 CDRH3 sequence
GILLNGIGAFDY → G to A
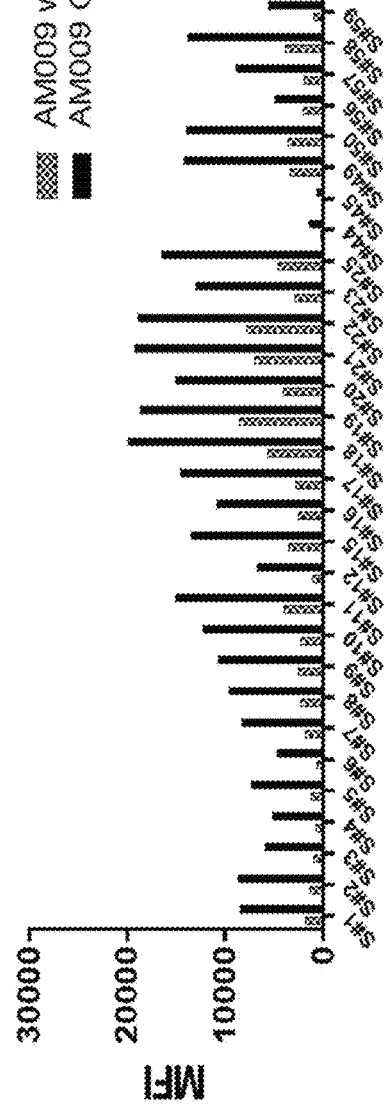
Fig. 4B
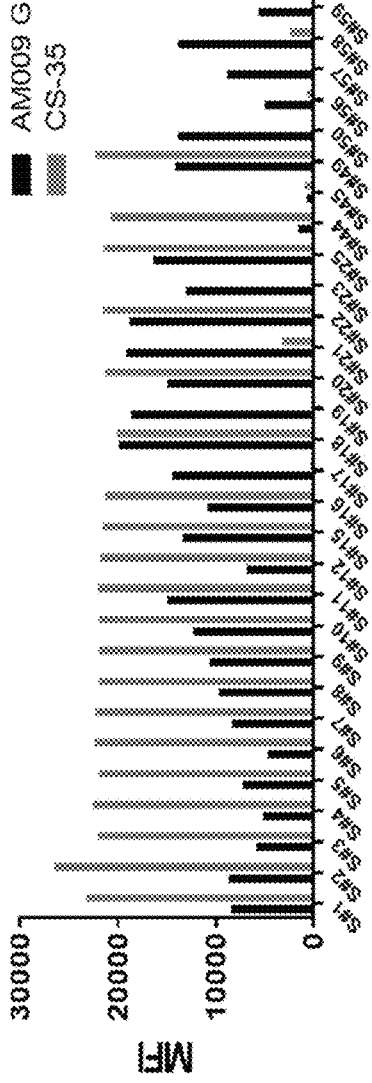
Fig. 4C

SEQUENCE LISTING

```
Sequence total quantity: 45
SEQ ID NO: 1           moltype = AA  length = 5
FEATURE                Location/Qualifiers
source                 1..5
                       mol_type = protein
```

```
SEQUENCE: 1
TYWIH                                                                 5

SEQ ID NO: 2            moltype = AA  length = 17
FEATURE                 Location/Qualifiers
source                  1..17
                        mol_type = protein
                        organism = Homo sapiens
SEQUENCE: 2
WIIPKSGGTN YAQKFQG                                                   17

SEQ ID NO: 3            moltype = AA  length = 12
FEATURE                 Location/Qualifiers
source                  1..12
                        mol_type = protein
                        organism = Homo sapiens
SEQUENCE: 3
GILLNGIGAF DY                                                        12

SEQ ID NO: 4            moltype = AA  length = 11
FEATURE                 Location/Qualifiers
source                  1..11
                        mol_type = protein
                        organism = Homo sapiens
SEQUENCE: 4
RTSQTVSSNL N                                                         11

SEQ ID NO: 5            moltype = AA  length = 7
FEATURE                 Location/Qualifiers
source                  1..7
                        mol_type = protein
                        organism = Homo sapiens
SEQUENCE: 5
GISDLHS                                                               7

SEQ ID NO: 6            moltype = AA  length = 9
FEATURE                 Location/Qualifiers
source                  1..9
                        mol_type = protein
                        organism = Homo sapiens
SEQUENCE: 6
QQSYSLPRT                                                             9

SEQ ID NO: 7            moltype = AA  length = 5
FEATURE                 Location/Qualifiers
source                  1..5
                        mol_type = protein
                        organism = Homo sapiens
SEQUENCE: 7
DYYIH                                                                 5

SEQ ID NO: 8            moltype = AA  length = 17
FEATURE                 Location/Qualifiers
source                  1..17
                        mol_type = protein
                        organism = Homo sapiens
SEQUENCE: 8
WINPHSGDTN SAQKFQG                                                   17

SEQ ID NO: 9            moltype = AA  length = 14
FEATURE                 Location/Qualifiers
source                  1..14
                        mol_type = protein
                        organism = Homo sapiens
SEQUENCE: 9
DHYYDTSAYN PSDF                                                      14

SEQ ID NO: 10           moltype = AA  length = 11
FEATURE                 Location/Qualifiers
source                  1..11
                        mol_type = protein
                        organism = Homo sapiens
SEQUENCE: 10
RTSQSVSSNL A                                                         11
```

```
SEQ ID NO: 11              moltype = AA   length = 7
FEATURE                    Location/Qualifiers
source                     1..7
                           mol_type = protein
                           organism = Homo sapiens
SEQUENCE: 11
DASNRAT                                                                    7

SEQ ID NO: 12              moltype = AA   length = 10
FEATURE                    Location/Qualifiers
source                     1..10
                           mol_type = protein
                           organism = Homo sapiens
SEQUENCE: 12
QQRTHWPPFT                                                                10

SEQ ID NO: 13              moltype = AA   length = 121
FEATURE                    Location/Qualifiers
source                     1..121
                           mol_type = protein
                           organism = Homo sapiens
SEQUENCE: 13
QVQLVESGAE VKKPGASVKV SCKASGYTFS TYWIHWMRQA PGQGPEWMGW IIPKSGGTNY          60
AQKFQGRVAM TRDTSLNTVY MELSRLTSDD TAVYYCARGI LLNGIGAFDY WGQGTLVTVS         120
S                                                                        121

SEQ ID NO: 14              moltype = AA   length = 121
FEATURE                    Location/Qualifiers
source                     1..121
                           mol_type = protein
                           organism = Homo sapiens
SEQUENCE: 14
QVQLVESGAE VKKPGASVKV SCKASGYTFA TYWIHWMRQA PGQGPEWMGW IIPKSGGTNY          60
AQKFQGRVAM TRDTSLNTVY MELSRLTSDD TAVYYCARGI LLNGIGAFDY WGQGTLVTVS         120
S                                                                        121

SEQ ID NO: 15              moltype = AA   length = 107
FEATURE                    Location/Qualifiers
source                     1..107
                           mol_type = protein
                           organism = Homo sapiens
SEQUENCE: 15
DIVMTQSPSS LSASVGDRVT ITCRTSQTVS SNLNWYQQRP GKAPKLLISG ISDLHSGVPS          60
RFSGSGSGTD FTLTISSLQP EDSATYYCQQ SYSLPRTFGQ GTKVEIK                      107

SEQ ID NO: 16              moltype = AA   length = 121
FEATURE                    Location/Qualifiers
source                     1..121
                           mol_type = protein
                           organism = Homo sapiens
SEQUENCE: 16
QVQLVESGAE VKKPGASVKV SCKASGFTFT DYYIHWVRQA PGQGLEWIGW INPHSGDTNS          60
AQKFQGRVTM TRDTSISTAY MELSRLRSYD TAVYYCARGI LLNGIGAFDY WGQGTLVTVS         120
S                                                                        121

SEQ ID NO: 17              moltype = AA   length = 108
FEATURE                    Location/Qualifiers
source                     1..108
                           mol_type = protein
                           organism = Homo sapiens
SEQUENCE: 17
EIVLTQSPAT LSLSPGERAT LSCRTSQSVS SNLAWYQQKA GQTPRLIIYD ASNRATGTPA          60
RFSGSGSGTD FTLTISSLEP EDFAVYYCQQ RTHWPPFTFG GGTKVEIK                     108

SEQ ID NO: 18              moltype = AA   length = 121
FEATURE                    Location/Qualifiers
source                     1..121
                           mol_type = protein
                           organism = Homo sapiens
SEQUENCE: 18
QVQLVESGAE VKKPGASVKV SCKASGFTFT DYYIHWVRQA PGQGLEWIGW INPHSGDTNS          60
AQKFQGRVTM TRDTSISTAY MELSRLRSYD TAVYYCSRGI LLNGIGAFDY WGQGTLVTVS         120
S                                                                        121

SEQ ID NO: 19              moltype = AA   length = 121
FEATURE                    Location/Qualifiers
source                     1..121
                           mol_type = protein
                           organism = Homo sapiens
```

```
SEQUENCE: 19
QVQLVESGAE VKKPGASVKV SCKASGYTFS TYWIHWMRQA PGQGPEWMGW IIPKSGGTNY    60
AQKFQGRVAM TRDTSLNTVY MELSRLTSDD TAVYYCARGI LLNGIAAFDY WGQGTLVTVS   120
S                                                                  121

SEQ ID NO: 20              moltype = AA   length = 121
FEATURE                    Location/Qualifiers
source                     1..121
                           mol_type = protein
                           organism = Homo sapiens
SEQUENCE: 20
QVQLVESGAE VKKPGASVKV SCKASGYTFA TYWIHWMRQA PGQGPEWMGW IIPKSGGTNY    60
AQKFQGRVAM TRDTSLNTVY MELSRLTSDD TAVYYCARGI LLNGIAAFDY WGQGTLVTVS   120
S                                                                  121

SEQ ID NO: 21              moltype = AA   length = 8
FEATURE                    Location/Qualifiers
SITE                       5
                           note = MISC_FEATURE - X = A or S
source                     1..8
                           mol_type = protein
                           organism = Homo sapiens
SEQUENCE: 21
GYTFXTYW                                                             8

SEQ ID NO: 22              moltype = AA   length = 8
FEATURE                    Location/Qualifiers
source                     1..8
                           mol_type = protein
                           organism = Homo sapiens
SEQUENCE: 22
IIPKSGGT                                                             8

SEQ ID NO: 23              moltype = AA   length = 14
FEATURE                    Location/Qualifiers
source                     1..14
                           mol_type = protein
                           organism = Homo sapiens
SEQUENCE: 23
ARGILLNGIG AFDY                                                     14

SEQ ID NO: 24              moltype = AA   length = 6
FEATURE                    Location/Qualifiers
source                     1..6
                           mol_type = protein
                           organism = Homo sapiens
SEQUENCE: 24
QTVSSN                                                               6

SEQ ID NO: 25              moltype = AA   length = 9
FEATURE                    Location/Qualifiers
source                     1..9
                           mol_type = protein
                           organism = Homo sapiens
SEQUENCE: 25
QQSYSLPRT                                                            9

SEQ ID NO: 26              moltype = AA   length = 8
FEATURE                    Location/Qualifiers
source                     1..8
                           mol_type = protein
                           organism = Homo sapiens
SEQUENCE: 26
GFTFTDYY                                                             8

SEQ ID NO: 27              moltype = AA   length = 8
FEATURE                    Location/Qualifiers
source                     1..8
                           mol_type = protein
                           organism = Homo sapiens
SEQUENCE: 27
INPHSGDT                                                             8

SEQ ID NO: 28              moltype = AA   length = 16
FEATURE                    Location/Qualifiers
source                     1..16
                           mol_type = protein
                           organism = Homo sapiens
```

```
SEQUENCE: 28
SRDHYYDTSA YNPSDF                                                       16

SEQ ID NO: 29           moltype = AA  length = 6
FEATURE                 Location/Qualifiers
source                  1..6
                        mol_type = protein
                        organism = Homo sapiens
SEQUENCE: 29
QSVSSN                                                                   6

SEQ ID NO: 30           moltype = AA  length = 10
FEATURE                 Location/Qualifiers
source                  1..10
                        mol_type = protein
                        organism = Homo sapiens
SEQUENCE: 30
QQRTHWPPFT                                                              10

SEQ ID NO: 31           moltype = AA  length = 14
FEATURE                 Location/Qualifiers
source                  1..14
                        mol_type = protein
                        organism = Homo sapiens
SEQUENCE: 31
ARGILLNGIA AFDY                                                         14

SEQ ID NO: 32           moltype = AA  length = 14
FEATURE                 Location/Qualifiers
source                  1..14
                        mol_type = protein
                        organism = Homo sapiens
SEQUENCE: 32
SRGILLNGIG AFDY                                                         14

SEQ ID NO: 33           moltype = AA  length = 123
FEATURE                 Location/Qualifiers
source                  1..123
                        mol_type = protein
                        organism = Homo sapiens
SEQUENCE: 33
QVQLVESGAE VKKPGASVKV SCKASGFTFT DYYIHWVRQA PGQGLEWIGW INPHSGDTNS        60
AQKFQGRVTM TRDTSISTAY MELSRLRSYD TAVYYCSRDH YYDTSAYNPS DFWGQGTLVT       120
VSS                                                                    123

SEQ ID NO: 34           moltype = DNA  length = 363
FEATURE                 Location/Qualifiers
source                  1..363
                        mol_type = unassigned DNA
                        organism = Homo sapiens
SEQUENCE: 34
caggtgcagc tggtggagtc tggggctgag gtgaagaagc ctggggcctc agtgaaggtc        60
tcctgcaagg cttctgggta caccttctcc acctactgga tccactggat gcggcaggcc       120
cctggacaag ggcctgagtg gatggggtgg atcatcccta agagtggcgg cacaaactat       180
gcacagaagt tcagggcag ggtcgccatg accaggaca cgtccctcaa tacagtctac        240
atggagttga gcaggctgac atcgacgac acggccgttt attattgtgc gagaggtatt       300
ctgttgaacg gaattggggc cttigactac tggggccagg aaccctggt caccgtctcc      360
tca                                                                    363

SEQ ID NO: 35           moltype = DNA  length = 363
FEATURE                 Location/Qualifiers
source                  1..363
                        mol_type = unassigned DNA
                        organism = Homo sapiens
SEQUENCE: 35
caggtgcagc tggtggagtc tggggctgag gtgaagaagc ctggggcctc agtgaaggtc        60
tcctgcaagg cttctgggta caccttcgcc acctactgga tccactggat gcggcaggcc       120
cctggacaag ggcctgagtg gatggggtgg atcatcccta agagtggcgg cacaaactat       180
gcacagaagt tcagggcag ggtcgccatg accaggaca cgtccctcaa tacagtctac        240
atggagttga gcaggctgac atcgacgac acggccgttt attattgtgc gagaggtatt       300
ctgttgaacg gaattggggc cttigactac tggggccagg aaccctggt caccgtctcc      360
tca                                                                    363

SEQ ID NO: 36           moltype = DNA  length = 321
FEATURE                 Location/Qualifiers
source                  1..321
                        mol_type = unassigned DNA
                        organism = Homo sapiens
```

SEQUENCE: 36
gatattgtga tgacccagtc tccatcctcc ctgtccgcat ctgttggaga cagagtcacc     60
atcacttgcc ggacgagtca gaccgtttcc agtaatttaa attggtatca gcagagacca    120
gggaaagccc ctaaactcct gatctctggt atatccgatc tgcatagtgg ggtcccatca    180
aggttcagtg gcagtgggtc tgggacagat ttcactctca ccatcagcag tctgcagcct    240
gaagattctg caacttacta ctgtcaacag agttacagtc ccctcggac gttcggccaa     300
gggaccaagg tggaaatcaa a                                              321

SEQ ID NO: 37           moltype = DNA   length = 369
FEATURE                 Location/Qualifiers
source                  1..369
                        mol_type = unassigned DNA
                        organism = Homo sapiens
SEQUENCE: 37
caggtacagc tggtggagtc tggggctgag gtgaagaagc ctggggcctc agtgaaggtc     60
tcctgcaagg cttctggatt caccttcacc gactactata tacactgggt gcgacaggcc    120
cctggacaag gcttgagtg gattggatgg atcaaccctc acagtggtga cacaaactct     180
gcacagaagt tcagggcag ggtcaccatg accagggaca cgtccatcag cacagcctac     240
atggagctga gcaggctgag atcttacgac acggccgtct attactgttc gagagatcac    300
tactatgata ctagtgctta taaccccagt gacttctggg gccagggaac cctggtcacc    360
gtctcctca                                                            369

SEQ ID NO: 38           moltype = DNA   length = 324
FEATURE                 Location/Qualifiers
source                  1..324
                        mol_type = unassigned DNA
                        organism = Homo sapiens
SEQUENCE: 38
gaaattgtgt tgacgcagtc tccagccacc ctgtctttgt ctccagggga aagagccacc     60
ctctcctgta ggaccagtca gagtgttagc agcaacttag gcagaaagcct ctgtacca     120
ggccagactc ccaggctcat catctatgat gcatccaaca gggccactgg caccccagcc    180
aggttcagtg gcagtgggtc tgggacagac ttcactctca ccatcagcag cctagagcct    240
gaagattttg cggtttatta ctgtcagcag cgtacccact ggcctccgtt cactttcggc    300
ggagggacca aggtggaaat caaa                                           324

SEQ ID NO: 39           moltype = DNA   length = 365
FEATURE                 Location/Qualifiers
source                  1..365
                        mol_type = unassigned DNA
                        organism = Homo sapiens
SEQUENCE: 39
caggtacagc tggtggagtc tggggctgag gtgaagaagc ctggggcctc agtgaaggtc     60
tcctgcaagg cttctggatt caccttcacc gactactata tacactgggt gcgacaggcc    120
cctggacaag gcttgagtg gattggatgg atcaaccctc acagtggtga cacaaactct     180
gcacagaagt tcagggcag ggtcaccatg accagggaca cgtccatcag cacagcctac     240
atggagctga gcaggctgag atcttacgac acggccgtct attactgtgc gagaggtatt    300
ctgttgaacg gaattggggc ctttgactac tggggccagg gaaccctggt caccgtctcc    360
tcagc                                                                365

SEQ ID NO: 40           moltype = DNA   length = 365
FEATURE                 Location/Qualifiers
source                  1..365
                        mol_type = unassigned DNA
                        organism = Homo sapiens
SEQUENCE: 40
caggtacagc tggtggagtc tggggctgag gtgaagaagc ctggggcctc agtgaaggtc     60
tcctgcaagg cttctggatt caccttcacc gactactata tacactgggt gcgacaggcc    120
cctggacaag gcttgagtg gattggatgg atcaaccctc acagtggtga cacaaactct     180
gcacagaagt tcagggcag ggtcaccatg accagggaca cgtccatcag cacagcctac     240
atggagctga gcaggctgag atcttacgac acggccgtct attactgttc gagaggtatt    300
ctgttgaacg gaattggggc ctttgactac tggggccagg gaacccctggt caccgtctcc   360
tcagc                                                                365

SEQ ID NO: 41           moltype = DNA   length = 363
FEATURE                 Location/Qualifiers
source                  1..363
                        mol_type = unassigned DNA
                        organism = Homo sapiens
SEQUENCE: 41
caggtgcagc tggtggagtc tggggctgag gtgaagaagc ctggggcctc agtgaaggtc     60
tcctgcaagg cttctgggta caccttctcc acctactgga tccactggat gcggcaggcc    120
cctggacaag gcctgagtg gatggggtgg atcatcccta agagtggcgg cacaaactat    180
gcacagaagt tcagggcag ggtcgccatg accagggaca cgtccctcaa tacagtgtac    240
atggagttga gcaggctgac atcggacgac acggccgttt attattgtgc gagaggtatt    300
ctgttgaacg gaattgcggc ctttgactac tggggccagg gaaccctggt caccgtctcc    360
tca                                                                  363

SEQ ID NO: 42           moltype = DNA   length = 363
FEATURE                 Location/Qualifiers

```
source              1..363
                    mol_type = unassigned DNA
                    organism = Homo sapiens
SEQUENCE: 42
caggtgcagc tggtggagtc tggggctgag gtgaagaagc ctggggcctc agtgaaggtc    60
tcctgcaagg cttctgggta caccttcgcc acctactgga tccactggat gcggcaggcc   120
cctggacaag ggcctgagtg gatggggtgg atcatcccta agagtggcgg cacaaactat   180
gcacagaagt tcagggcag ggtcgccatg accagggaca cgtccctcaa tacagtctac    240
atggagttga gcaggctgac atcggacgac acggccgttt attattgtgc gagaggtatt   300
ctgttgaacg gaattgcggc ctttgactac tggggccagg gaaccctggt caccgtctcc   360
tca                                                                 363

SEQ ID NO: 43       moltype = AA  length = 98
FEATURE             Location/Qualifiers
source              1..98
                    mol_type = protein
                    organism = Homo sapiens
SEQUENCE: 43
QVQLVQSGAE VKKPGASVKV SCKASGYTFT GYYMHWVRQA PGQGLEWMGW INPNSGGTNY    60
AQKFQGRVTM TRDTSISTAY MELSRLRSDD TAVYYCAR                            98

SEQ ID NO: 44       moltype = AA  length = 98
FEATURE             Location/Qualifiers
source              1..98
                    mol_type = protein
                    organism = Homo sapiens
SEQUENCE: 44
DIQMTQSPSS LSASVGDRVT ITCRASQSIS SYLNWYQQKP GKAPKLLIYA ASSLQSGVPS    60
RFSGSGSGTD FTLTISSLQP EDFATYYCQQ SYSTPEIK                            98

SEQ ID NO: 45       moltype = AA  length = 12
FEATURE             Location/Qualifiers
source              1..12
                    mol_type = protein
                    organism = Homo sapiens
SEQUENCE: 45
GILLNGIAAF DY                                                        12
```

HIGH-AFFINITY *MYCOBACTERIUM TUBERCULOSIS* CAPSULE-SPECIFIC HUMAN MONOCLONAL ANTIBODY

CROSS-REFERENCE TO RELATED APPLICATIONS

This application is a Divisional of U.S. application Ser. No. 17/247,532, filed Dec. 15, 2020, issued as U.S. Pat. No. 11,643,455 on May 9, 2023, which is a Continuation-In-Part of U.S. application Ser. No. 17/047,256, filed Oct. 13, 2020, which is a 371 Application of PCT/US2019/027218, filed Apr. 12, 2019, which claims priority under 35 U.S.C. § 119(e) to U.S. Provisional Application Ser. No. 62/657,253 filed Apr. 13, 2018 and U.S. Provisional Application Ser. No. 62/739,428 filed Oct. 1, 2018, the disclosures of which are incorporated herein in their entireties.

STATEMENT OF GOVERNMENT SUPPORT

This invention was made with government support under grant numbers AI125462 and AI127173 awarded by the National Institutes of Health. The government has certain rights in the invention.

SEQUENCE LISTING

This application contains a Sequence Listing which has been submitted electronically in xml format and is hereby incorporated by reference in its entirety. Said xml copy, created on Apr. 28, 2023, is named "Seq Listing 182219.00178.xml" and is 21,504 bytes in size.

FIELD OF THE INVENTION

This disclosure relates generally to antibodies against *Mycobacterium tuberculosis* capsular polysaccharides and methods of use thereof.

BACKGROUND OF THE INVENTION

With over 10 million cases per year and one million associated deaths, active tuberculosis (TB), caused by the facultative intracellular *Mycobacterium tuberculosis* (Mtb), is, after COVID-19, the leading cause of death from a single infectious agent. While an estimated quarter of the world is latently infected with Mtb, TB is caused by uncontrolled infection leading to a predominantly respiratory and transmissible disease.

The capsule of microorganisms, including Mtb, is an important virulence factor. Antibodies (Abs) to capsular and surface polysaccharides are protective against infections with encapsulated extra- and intracellular pathogens. Some successful vaccines are based on inducing Abs to capsular polysaccharides. The mechanisms by which Abs protect against *Mycobacterium tuberculosis* (Mtb) have been insufficiently studied because of the general belief that Mtb, a predominantly intracellular organism, is outside the reach of extracellular located Abs. However, Abs contribute to the defense against many intracellular pathogens, including Mtb, through various functions, including interactions with Fc receptors (FcR) and the modulation of innate and other immune responses.

The majority of the mycobacterial capsule is composed of proteins and polysaccharides; lipids are a minor component of the capsule. The three major capsular polysaccharides are α-glucan, arabinomannan (AM) and mannan. The 13-20 kDa, immunogenic polysaccharide AM can be isolated from the capsule of Mtb. AM is structurally related to lipoarabinomannan (LAM), a glycolipid from the cell walls and membranes of mycobacteria, and both AM and LAM are very immunogenic. Some but not all murine monoclonal antibodies (mAbs) to AM/LAM show protective in vivo efficacy, and immunization with AM/LAM-protein conjugates improves the outcome of Mtb infected mice. However, these studies are limited in capturing the tremendous complexity and heterogeneity of potentially Mtb protective antibodies in humans. Nevertheless, they are consistent with the data that not all 'anti-AM' mAbs have the same binding specificity or protective ability. Several recent studies provide compelling data suggesting that Mtb specific antibodies have a role in controlling Mtb infection in humans and could be protective but very little is known about the functions of antigen-specific human mAbs in Mtb infection.

Accordingly, to combat the major global public health problem caused by TB, ongoing development of additional tools for both research and clinical care is critical to meet the continuing urgent need for the rapid detection, treatment, and prevention of Mtb infection. Beyond their potential to inform vaccine and immunotherapy development, antibodies are versatile and indispensable tools in a plethora of applications in medicine and research, including the detection of pathogens and their antigens.

BRIEF SUMMARY OF THE INVENTION

An anti-*Mycobacterium tuberculosis* arabinomannan (anti-Mtb AM) antibody, or *Mycobacterium tuberculosis* arabinomannan-binding fragment (Mtb AM-binding fragment) thereof, is provided, wherein said antibody or fragment thereof:
(a) (i) comprises VH complementarity determining region-3 (CDRH3) amino acid sequence of SEQ ID NO: 3, but (ii) does not comprise complementarity determining region-1 (CDRH1) of SEQ ID NO:1 or does not comprise complementarity determining region-1 (CDRH2) of SEQ ID NO:2; or
(b) (i) comprises VH complementarity determining region-3 (CDRH3) amino acid sequence of SEQ ID NO: 23, but (ii) does not comprise complementarity determining region-1 (CDRH1) of SEQ ID NO:21 or does not comprise complementarity determining region-1 (CDRH2) of SEQ ID NO:22; or
(c) comprises VH complementarity determining region-3 (CDRH3) amino acid sequence of SEQ ID NO: 31; or
(d) comprises VH complementarity determining region-3 (CDRH3) amino acid sequence of SEQ ID NO: 32.

An anti-*Mycobacterium tuberculosis* arabinomannan (anti-Mtb AM) antibody, or *Mycobacterium tuberculosis* arabinomannan-binding fragment thereof, is provided, wherein said antibody or fragment thereof comprises:
(i) VH complementarity determining region (CDR) amino acid sequences o SEQ ID NOS: 1, 2 and 9; or SEQ ID NOS: 7, 8 and 3; or SEQ ID NOS: 21, 22 and 28; or SEQ ID NOS: 26, 27 and 23; or SEQ ID NOS: 21, 22 and 31; or SEQ ID NOS: 21, 22 and 32; or SEQ ID NOS: 7, 8 and 32, and
(ii) VL CDR amino acid sequences SEQ ID NOS: 4, 5 and 6; or SEQ ID NOS: 10, 11 and 12; or SEQ ID NO: 24, the sequence GIS and SEQ ID NO: 25; or SEQ ID NO: 29, the sequence DAS and SEQ ID NO: 30; or SEQ ID NOS: 21, 22 and 32.

An nucleic acid molecule encoding the antibody, or Mtb AM-binding fragment thereof, described herein is provided.

In an embodiment, the nucleic acid is a DNA. In an embodiment, the nucleic acid is a cDNA. In an embodiment, the nucleic acid is an RNA.

A vector encoding the nucleic acid molecule described herein is provided. A host cell comprising the nucleic acid molecule described herein, or the vector described herein, is provided.

A method of producing an anti-Mtb AM antibody, or Mtb AM-binding fragment thereof, comprising culturing the host cell described herein, under conditions wherein the anti-Mtb AM antibody, or Mtb AM-binding fragment thereof, is produced by the host cell, is provided herein.

A pharmaceutical composition comprising an anti-Mtb AM antibody, or Mtb AM-binding fragment thereof, described herein, and a pharmaceutically acceptable excipient, is provided.

A method of reducing an activity of Mtb AM in a subject in need thereof is provided, comprising administering to said subject a therapeutically effective amount of the anti-Mtb AM antibody, or Mtb AM-binding fragment thereof, as described herein.

A method of treating a *Mycobacterium tuberculosis* infection in a subject, comprising administering to the subject an amount of the anti-Mtb AM antibody, or Mtb AM-binding fragment thereof, as described herein, or the pharmaceutical composition described herein, effective to treat a *Mycobacterium tuberculosis* infection, is provided herein.

A method of reducing the likelihood of an *Mycobacterium tuberculosis* infection in a subject, comprising administering to the subject who does not have a *Mycobacterium tuberculosis* infection an amount of the anti-Mtb AM antibody, or Mtb AM-binding fragment thereof, as described herein, or the pharmaceutical composition described herein, effective to reduce the likelihood of an *Mycobacterium tuberculosis* infection, is provided herein.

A method of treating a disease, disorder, or condition mediated by, or related to increased activity of *Mycobacterium tuberculosis* in a subject, comprising administering to said subject a therapeutically effective amount of the anti-Mtb AM antibody, or Mtb AM-binding fragment thereof, as described herein, or the pharmaceutical composition described herein, is provided herein.

An assay device is provided for selectively detecting one or more bacteria from the *Mycobacterium tuberculosis* complex (MTC) group in a biological sample comprising: a first portion comprising a first plurality of anti-Mtb AM-antibodies, or Mtb AM-binding fragments thereof, as described herein, or anti-mycobacterial AM-antibodies, wherein the antibodies or fragments are each attached to their own reporting entity; and a second portion comprising a second plurality of anti-Mtb AM-antibodies, or Mtb AM-binding fragments thereof, or anti-mycobacterial AM-antibodies.

Also provided is a lateral flow assay device for detecting one or more bacteria from the MTC group in a biological sample comprising: a first portion comprising a first plurality of anti-Mtb AM-antibodies, or Mtb AM-binding fragments thereof, as described herein; comprising a heavy chain variable region of SEQ ID NOS: 13 or 14 and a light chain variable region of SEQ ID NO:15; or comprising a heavy chain variable region of SEQ ID NO: 33 and a light chain variable region of SEQ ID NO:17, wherein the antibodies or fragments thereof are each attached to their own reporting entity; and a second portion comprising a second plurality of anti-Mtb AM antibodies, or Mtb AM-binding fragments thereof, or anti-mycobacterial AM-antibodies.

BRIEF DESCRIPTION OF THE DRAWINGS

FIGS. 1A, 1B, 1C, 1D, and 1E show that anti-AM IgG titers in sera significantly correlate with mycobacteria phagocytosis, growth rate, and reactivity to certain AM OS fragments. (adapted from Chen, et al. 2016, *J. Infect. Dis.* 214(2) 300-10). FIG. 1A shows anti-AM IgG responses after primary BCG vaccination increases Wilcoxon matched-pairs signed rank test. FIG. 1B shows the significant correlation between 4 weeks post-vaccination IgG responses to AM and enhanced BCG phagocytosis (in fold change compared to co-incubation with pre-vaccination sera) by THP-1 cells co-incubated with corresponding 4 weeks post-vaccination sera using Spearman rank correlation test. FIG. 1C shows the significant BCG growth reduction in THP-1 cells incubated with post-compared to pre-vaccination sera. FIG. 1D shows the correlation between 8 weeks post-vaccination IgG titers and mycobacterial growth reduction using the Spearman rank correlation test. FIG. 1E shows the significant correlations between increased IgG reactivity to certain AM epitopes at 4 weeks post vaccination and enhanced BCG phagocytosis by human macrophages co-incubated with corresponding sera.

FIGS. 2A, 2B, 2C, and 2D show that serum from a PPD+ subject, coded V57, in the presence of AM-specific IgG has protective functions in vitro and in vivo. FIG. 2A shows V57 serum recognition of AM oligosaccharides before depletion and after depletion of AM-specific IgG. FIG. 2B shows the decrease in Mtb phagocytosis after serum is depleted of AM-specific IgG.

FIG. 2C shows the increase in intracellular Mtb growth after serum is depleted of AM-specific IgG. FIG. 2D shows that V57 serum decreases the bacterial burden in the lungs of mice infected with Mtb. Adapted from Chen et al., J Clin Invest. 2020 Apr. 1; 130(4):1808-1822.

FIGS. 3A, 3B, 3C, 3D, and 3E depict the characterization of monoclonal antibody (mAb) AM009's binding properties (AM009 is also known as T1AM09). FIG. 3A shows mAb AM009 binds whole Mtb bacteria with higher affinity than other anti-AM mAbs by whole bacteria ELISA. FIG. 3B shows that AM009 in an IgG1 or IgG2 backbone significantly enhances opsonophagocytosis of Mtb; *$p<0.05$ one-way ANOVA; Mann-Whitney. FIG. 3C shows germline and mutation frequency information for AM009. FIG. 3D shows that AM009 binds with increased specificity to capsular arabinomannan (AM) isolated and purified from Mtb (strain H37Rv) compared to other surface polysaccharide components. FIG. 3E shows that TRITC-labeled anti-human IgG was used to detect AM009 binding to Mtb with an intact capsule (H37Rv grown without detergent).

FIGS. 4A, 4B, 4C, and 4D show that a point mutation in the CDRH3 increases the affinity of mAb AM009 (also known as T1AM09). FIG. 4A is a schematic of alanine scanning of AM009 CDRH3 (GILLNGIGAFDY, SEQ ID NO:3) showing that point mutation G100b to A100b (GILLNGIAAFDY, SEQ ID NO:45) is important for binding of AM009 to AM. FIG. 4B shows that the mean fluorescence intensity (MFI) on the synthetic AM oligosaccharide glycan array is increased in AM009 G100bA (m8) compared to AM009 (wt). FIG. 4C shows that the mAb recognition of oligosaccharide glycan fragments is distinct when AM009 G100bA (m8) is compared to murine mAb CS-35. This indicates that AM009 recognizes a different AM glycan epitope and has different binding properties than murine anti-LAM mAb CS-35. CS-35 is a murine mAb generated from *M. leprae* LAM. CS-35 cross-reacts with LAM and AM from many strains and is the standard positive control used in the field. FIG. 4D depicts raw images of the glycan array showing mAb binding reactivity to AM-OS fragments printed in triplicate.

FIG. 5A depicts Biolayer Interferometry (BLI) data showing the unusually high binding affinity of AM009 to the mycobacterial capsular polysaccharide arabinomannan (AM). Kinetic characterization of mAb-AM (H37Rv) interaction with solid lines representing experimental data and dashed lines representing the statistical fitting of curves is shown. The mutation in AM009 G100bA resulted in an overall higher affinity binding to AM. Data also show distinct binding kinetics of AM009 versus murine mAb CS-35. FIG. 5B shows MAb binding by ELISA to AM isolated from five mycobacterial strains. It shows that AM009 has greater specificity for AM isolated from virulent strains CDC1551 and H37Rv compared to AM isolated avirulent strains H37Ra and BCG. One-way ANVOA was used to test a group comparison of the EC50s from two independent experiments. AM009 G100bA and murine mAb, CS-35 show significant difference in binding AM from different mycobacterial strains FIG. 6A shows AM009 binding to virulent laboratory (H37Rv and Erdman) and clinical strains (CDC1551 and Beijing) of Mtb, avirulent strains of the Mtb complex group (H37Ra and BCG Pasteur) and non-tuberculosis mycobacteria (*M. avium* and *M. abscessus*). FIG. 6B shows binding of positive (sera from V57) and negative (isotype matched mAb F4 to a flavivirus) controls to H37Rv.

FIG. 8A shows detection of serial dilutions of LAM (generated from the clinical Mtb strain CDC1551) and spiked into urine by mAbs AM009 (also known as T1AM09), AM009 G100bA, and CS-35 (10 μg/ml) as a capture and A194 (250 ng/ml) as a detection mAb. FIG. 8B shows a combination of murine mAb CS-35 (10 μg/ml) as a capture and human mAbs AM009, AM009 G100bA, and A194 (250 ng/ml) as detection mAb. CS-35 and A194 are used as reference capture and detection mAbs, respectively.

FIG. 9F shows lack of staining of Mtb Erdman infected lung tissue by isotype matched control mAb F4 to a flavivirus (scale bar 500 μm).

DETAILED DESCRIPTION OF THE INVENTION

Figure 5A:
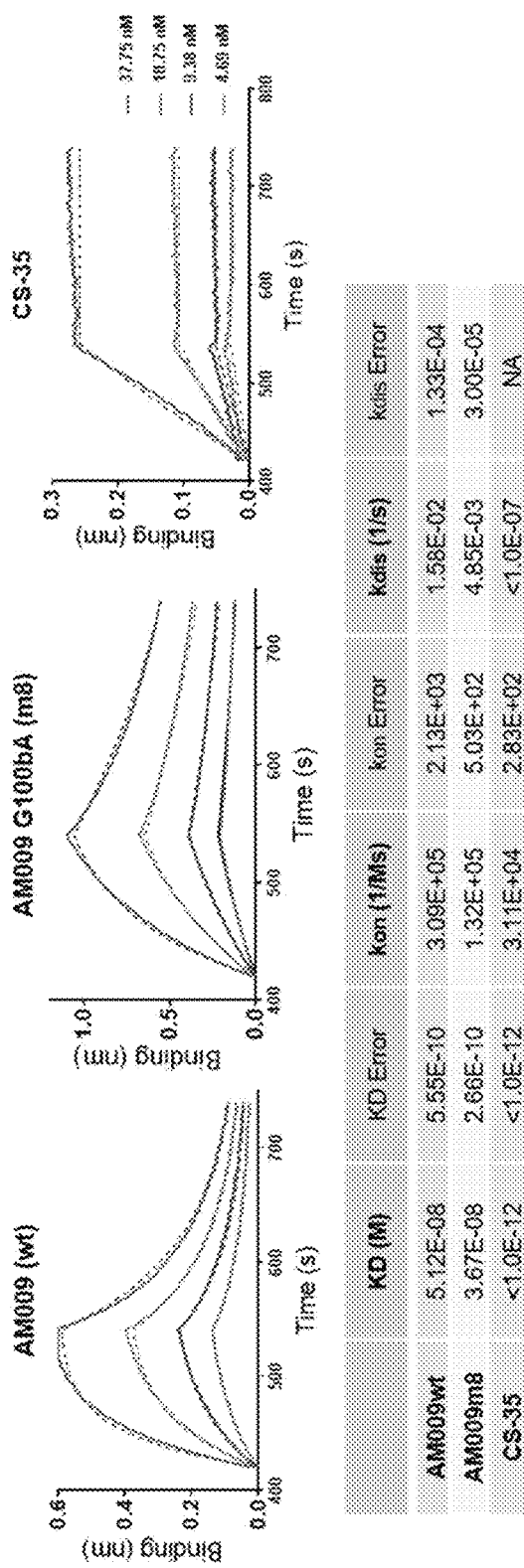
FIGS. 5A and 5B show that AM009 (also known as T1AM09) has novel binding kinetics and polysaccharide binding patterns specific for a glycan epitope in virulent H37Rv and CDC1551 AM.
Figure 5B:
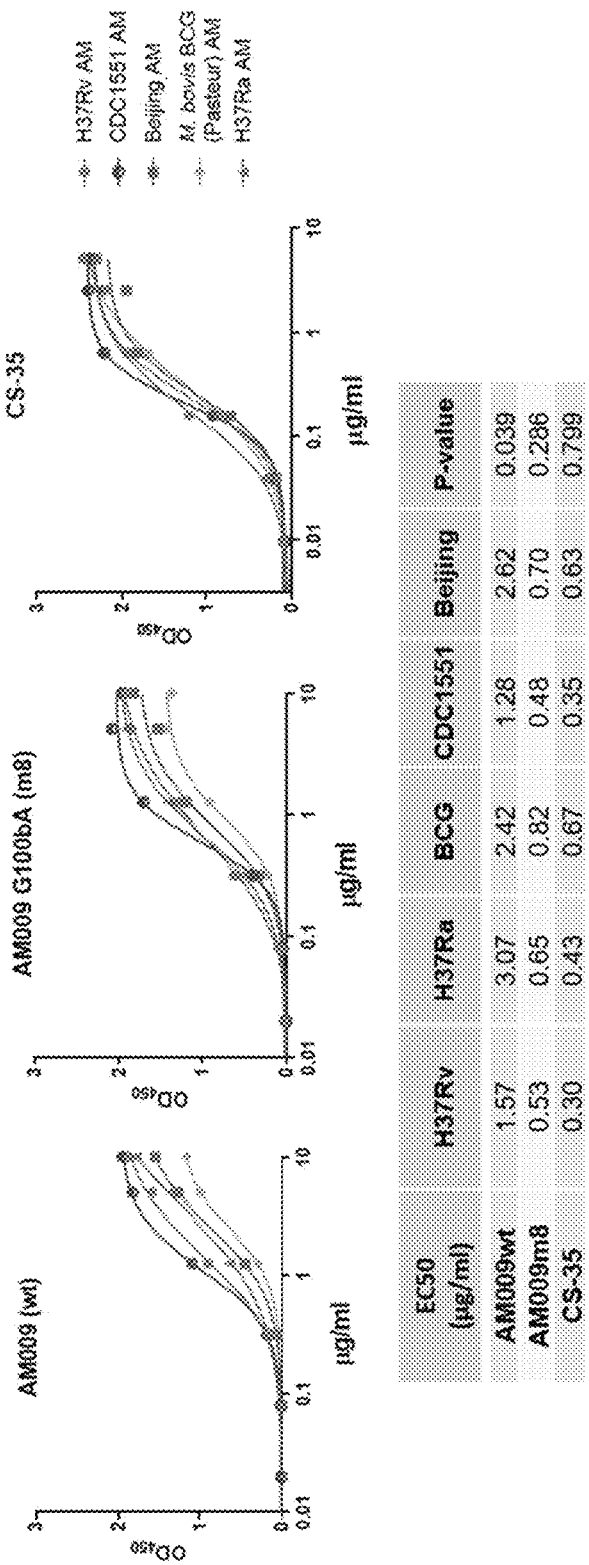

An anti-*Mycobacterium tuberculosis* arabinomannan (anti-Mtb AM) antibody, or *Mycobacterium tuberculosis* arabinomannan-binding fragment (Mtb AM-binding fragment) thereof, is provided, wherein said antibody or fragment thereof
(a) (i) comprises VH complementarity determining region-3 (CDRH3) amino acid sequence of SEQ ID NO: 3, but (ii) does not comprise complementarity determining region-1 (CDRH1) of SEQ ID NO:1 or does not comprise complementarity determining region-1 (CDRH2) of SEQ ID NO:2; or
(b) (i) comprises VH complementarity determining region-3 (CDRH3) amino acid sequence of SEQ ID NO: 23, but (ii) does not comprise complementarity determining region-1 (CDRH1) of SEQ ID NO:21 or does not comprise complementarity determining region-1 (CDRH2) of SEQ ID NO:22; or
(c) comprises VH complementarity determining region-3 (CDRH3) amino acid sequence of SEQ ID NO: 31; or
(d) comprises VH complementarity determining region-3 (CDRH3) amino acid sequence of SEQ ID NO: 32.

In embodiments, the anti-Mtb AM antibody or Mtb AM-binding fragment thereof, comprises VL CDR amino acid sequences of SEQ ID NOS: 4, 5 and 6; or SEQ ID NOS: 10, 11 and 12; or SEQ ID NO: 24, the sequence GIS and SEQ ID NO: 25; or SEQ ID NO: 29, the sequence DAS and SEQ ID NO: 30.

An anti-*Mycobacterium tuberculosis* arabinomannan (anti-Mtb AM) antibody, or *Mycobacterium tuberculosis* arabinomannan-binding fragment thereof, is provided, wherein said antibody or fragment thereof comprises:
(i) VH complementarity determining region (CDR) amino acid sequences of SEQ ID NOS: 1, 2 and 9; or SEQ ID NOS: 7, 8 and 3; or SEQ ID NOS: 21, 22 and 28; or SEQ ID NOS: 26, 27 and 23; or SEQ ID NOS: 21, 22 and 31; or SEQ ID NOS: 21, 22 and 32; SEQ ID NOS: 7, 8 and 32 and
(ii) VL CDR amino acid sequences of SEQ ID NOS: 4, 5 and 6; or SEQ ID NOS: 10, 11 and 12; or SEQ ID NO: 24, the sequence GIS and SEQ ID NO: 25; or SEQ ID NOS: 29, the sequence GIS and SEQ ID NO: 30.

In embodiments, the anti-Mtb AM antibody or Mtb AM-binding fragment thereof, comprises (i) VH CDR amino acid sequences of SEQ ID NOS: 7, 8 and 3; or SEQ ID NOS: 26, 27 and 23, and
(ii) VL CDR amino acid sequences of SEQ ID NOS: 4, 5 and 6; or SEQ ID NO: 29, the sequence DAS and SEQ ID NO: 30.

In embodiments, the anti-Mtb AM antibody or Mtb AM-binding fragment thereof, comprises (i) VH CDR amino acid sequences of SEQ ID NOS: 7, 8 and 32, and
(ii) VL CDR amino acid sequences of SEQ ID NOS: 10, 11 and 12; or SEQ ID NO: 29, the sequence DAS and SEQ ID NO: 30.

In embodiments, the anti-Mtb AM antibody or Mtb AM-binding fragment thereof, comprises (i) VH complementarity determining region (CDR) amino acid sequences of SEQ ID NOS: 21, 22 and 31, and
(ii) VL CDR amino acid sequences of SEQ ID NOS: 4, 5 and 6; or SEQ ID NOS: 10, 11 and 12; or SEQ ID NO: 24, the sequence GIS and SEQ ID NO: 25; or SEQ ID NO: 29, the sequence DAS and SEQ ID NO: 30.

In embodiments, the anti-Mtb AM antibody or Mtb AM-binding fragment thereof, comprises (i) VH complementarity determining region (CDR) amino acid sequences of SEQ ID NOS: 21, 22 and 31, wherein in SEQ ID NO: 21, X=A, and
  (ii) VL CDR amino acid sequences SEQ ID NO: 24, the sequence GIS and SEQ ID NO: 25.

In embodiments, the anti-Mtb AM antibody or Mtb AM-binding fragment thereof, comprises (i) VH complementarity determining region (CDR) amino acid sequences of SEQ ID NOS: 21, 22 and 31, wherein in SEQ ID NO: 21, X=S, and
  (ii) VL CDR amino acid sequences of SEQ ID NO: 24, the sequence GIS and SEQ ID NO: 25.

In embodiments, the antibody is a monoclonal antibody, or the fragment thereof is a fragment of a monoclonal antibody.

In embodiments, the anti-Mtb AM antibody or Mtb AM-binding fragment thereof, comprises (i) a VH framework comprising the framework sequence of human germline VH1-2*02; and/or (ii) a VL framework comprising the framework sequence of human germline IGKV1-39.

In embodiments, the anti-Mtb AM antibody or Mtb AM-binding fragment thereof, comprises a VH that comprises the amino acid sequence of SEQ ID NO: 16 or 18 or 19 or 20.

In embodiments, the anti-Mtb AM antibody or Mtb AM-binding fragment thereof, comprises a VL that comprises the amino acid sequence of SEQ ID NO: 15 or 17.

In embodiments, the anti-Mtb AM antibody or Mtb AM-binding fragment thereof, binds Mtb AM with a binding affinity (KD) of from about $1\times10^{-6}$ M to about $1\times10^{-9}$ M.

In embodiments, the anti-Mtb AM antibody or Mtb AM-binding fragment thereof, is a monoclonal antibody.

In embodiments, the anti-Mtb AM antibody or Mtb AM-binding fragment thereof, is a recombinant antibody.

In embodiments, the anti-Mtb AM antibody or Mtb AM-binding fragment thereof, has a human framework region.

In embodiments, the anti-Mtb AM antibody or Mtb AM-binding fragment thereof, has a human constant region or modified constant region. In some embodiments, the anti-Mtb AM antibody or Mtb AM-binding fragment thereof has a non-human constant region or a modified non-human constant region. In one embodiment, the anti-Mtb AM antibody or Mtb AM-binding fragment thereof has murine constant region or modified murine constant region. In one embodiment, the anti-Mtb AM antibody or Mtb AM-binding fragment thereof has a non-human primate constant region or modified non-human primate constant region.

Modified IgG Fc regions are well known in the art. For example, see any of the mutations listed in Table 1 of Wang et al. Protein Cell (2018), 9(1):63-73. In embodiments, the modified Fc region, relative to the unmodified Fc region, has enhanced complement-based effector function, increased or decreased FcγR-based effector function, reduced effector function, enhanced co-engagement of antigen and FcγRs, and/or increased serum half-life.

Examples of Fc modifications to modulate antibody effector function for IgG1 (see Wang et al. Protein Cell (2018), 9(1):63-73) included within the scope of the invention are:
  Increased FcγRIIIa binding: F243L/R292P/Y300L/V305I/P396L Increased FcγRIIIa binding: S239D/I332E
  Increased FcγRIIIa binding: decreased FcγRIIb binding S239D/I332E/A330L
  Increased FcγRIIIa binding S298A/E333A/K334A In one heavy chain: L234Y/L235Q/G236W/S239M/H268D/D270E/S298A and in the opposing heavy chain: D270E/K326D/A330M/K334E Increased FcγRIIa binding, increased FcγRIIIa binding G236A/S239D/I332E Enhance CDC
Increased C1q binding K326W/E333S
Increased C1q binding S267E/H268F/S324T Increased C1q binding IgG1/IgG3 cross subclass Hexamerization E345R/E430G/S440Y
Reduce effector function—Aglycosylated N297A or N297Q or N297G Reduced FcγR and C1q binding L235E
Reduced FcγR and C1q binding IgG1: L234A/L235A; IgG4:F234A/L235A Reduced FcγR and C1q binding IgG2/IgG4 cross isotype
Reduced FcγR and C1q binding IgG2: H268Q/V309L/A330S/P331S
Reduced FcγR and C1q binding IgG2: V234A/G237A/P238S/H268A/V309L/A330S/P331S
Increased FcRn binding at pH 6.0: M252Y/S254T/T256E
Increased FcRn binding at pH 6.0: M428L/N434S (Zalevsky et al., 2010)
Increased FcγRIIb binding: S267E/L328F (Chu et al., 2008)
Increased FcγRIIa binding, decreased FcγRIIIa binding: N325S/L328F.

In embodiments, an anti-Mtb AM antibody is provided.
In embodiments, an anti-Mtb AM-binding fragment of the antibody is provided.
In embodiments, the anti-Mtb AM-binding fragment is an Fab, F(ab)2 or scFv.

An isolated nucleic acid molecule encoding the antibody, or Mtb AM-binding fragment thereof, described herein is provided. In an embodiment, the nucleic acid is a DNA. In an embodiment, the nucleic acid is a cDNA. In an embodiment, the nucleic acid is an RNA.

In an embodiment, the disclosure provides a vector encoding the nucleic acid molecule described herein. In an embodiment, a host cell comprising the nucleic acid molecule described herein, or the vector described herein, is provided.

In an embodiment, the disclosure provides a method of producing an anti-Mtb AM antibody, or Mtb AM-binding fragment thereof, comprising culturing the host cell described herein under conditions wherein the anti-Mtb AM antibody, or Mtb AM-binding fragment thereof, is produced by the host cell.

In an embodiment, a pharmaceutical composition comprising an anti-Mtb AM antibody, or Mtb AM-binding fragment thereof, described herein, and a pharmaceutically acceptable excipient, is provided. The pharmaceutically acceptable excipient can be a pharmaceutically-acceptable material, composition or vehicle, such as a liquid or solid filler, diluent, manufacturing aid (e.g., lubricant, talc magnesium, calcium or zinc stearate, or steric acid), solvent or encapsulating material, involved in carrying or transporting the therapeutic compound for administration to the subject, bulking agent, salt, surfactant and/or a preservative. Some examples of materials which can serve as pharmaceutically-acceptable excipients include: sugars, such as lactose, glucose and sucrose; starches, such as corn starch and potato starch; cellulose and its derivatives, such as sodium carboxymethyl cellulose, ethyl cellulose and cellulose acetate; gelatin; talc; waxes; oils, such as peanut oil, cottonseed oil, safflower oil, sesame oil, olive oil, corn oil and soybean oil; glycols, such as ethylene glycol and propylene glycol; polyols, such as glycerin, sorbitol, mannitol and polyethylene glycol; esters, such as ethyl oleate and ethyl laurate; agar; buffering agents; water; isotonic saline; pH buffered solutions; and other non-toxic compatible substances employed in pharmaceutical formulations.

In some embodiments of the aspects described herein, the anti-Mtb AM antibody, or antigen-binding fragment thereof, is conjugated to a functional moiety. Examples of useful functional moieties include, but are not limited to, a blocking moiety, a detectable moiety, a diagnostic moiety, a targeting moiety, and a therapeutic moiety.

Exemplary blocking moieties include moieties of sufficient steric bulk and/or charge such that reduced glycosylation occurs, for example, by blocking the ability of a glycosidase to glycosyl-ate the antibody or antigen-binding fragment thereof. The blocking moiety may, additionally or alternatively, reduce effector function, for example, by inhibiting the ability of the Fc region to bind a receptor or complement protein. Preferred blocking moieties include cysteine adducts and PEG moieties.

In one embodiment, the blocking moiety is a cysteine, preferably a cysteine that has associated with a free cysteine, e.g., during or subsequent to the translation of the Fc containing polypeptide, e.g., in cell culture. Other blocking cysteine adducts include cystine, mixed disulfide ad-ducts, or disulfide linkages.

In another embodiment, the blocking moiety is a polyalkylene glycol moiety, for example, a PEG moiety and preferably a PEG-maleimide moiety. Preferred pegylation moieties (or related polymers) can be, for example, polyethylene glycol ("PEG"), polypropylene glycol ("PPG"), polyoxyethylated glycerol ("POG") and other polyoxyethylated polyols, polyvinyl alcohol ("PVA") and other polyalkylene oxides, polyoxyethylated sorbitol, or polyoxyethylated glu-cose. The polymer can be a homopolymer, a random or block copolymer, a terpolymer based on the monomers listed above, straight chain or branched, substituted or unsubstituted as long as it has at least one active sulfone moiety. The polymeric portion can be of any length or molecular weight but these characteristics can affect the biological properties. Polymer average molecular weights particularly useful for decreasing clearance rates in pharmaceutical applications are in the range of 2,000 to 35,000 Daltons. In addition, if two groups are linked to the polymer, one at each end, the length of the polymer can impact upon the effective distance, and other spatial relationships, between the two groups. Thus, one skilled in the art can vary the length of the polymer to optimize or confer the desired biological activity. PEG is useful in biological applications for several reasons. PEG typically is clear, colorless, odorless, soluble in water, stable to heat, inert to many chemical agents, does not hydrolyze, and is nontoxic. Pegylation can improve pharmacokinetic performance of a molecule by increasing the molecule's apparent molecular weight. The increased apparent molecular weight reduces the rate of clearance from the body following subcutaneous or systemic administration. In many cases, pegylation can decrease antigenicity and immunogenicity. In addition, pegylation can increase the solubility of a biologically-active molecule.

Examples of detectable moieties for the detection of the anti-Mtb AM antibodies and Mtb AM-binding fragments thereof contemplated by the disclosure include fluorescent moieties or labels, imaging agents, radioisotopic moieties, radiopaque moieties, and the like, e.g. detectable labels such as biotin, fluorophores, chromophores, spin resonance probes, or radiolabels. Exemplary fluorophores include fluorescent dyes (e.g. fluorescein, rhodamine, and the like) and other luminescent molecules (e.g. luminol). A fluorophore may be environmentally-sensitive such that its fluorescence changes if it is located close to one or more residues in the modified protein that undergo structural changes upon binding a substrate (e.g. dansyl probes). Exemplary radiolabels include small molecules containing atoms with one or more low sensitivity nuclei (13C, 15N, 2H, 125I, 123I, 99Tc, 43K, 52Fe, 67Ga, 68Ga, 111In and the like). Other useful moieties are known in the art.

Examples of therapeutic moieties include anti-tuberculosis agents. Anti-tuberculosis agents include, but are not limited to, ethambutol, pyrazinamide, streptomycin, isoniazid, moxifloxacin rifampicin, levofloxacin, moxifloxacin, clofazimine, bedaquiline, cycloserine, terizidone, delamanid, linezolid, pyrazinamide, imipenem-cilastatin (Ipm-Cln) or Meropenem, amikacin, streptomycin, ethionamide, Prothionamide, and p-aminosalicylic acid.

The functional moiety may also have one or more of the above-mentioned functions.

To increase the half-life of the antibodies or polypeptides containing the amino acid sequences described herein, one can attach a salvage receptor binding epitope to the anti-Mtb AM antibody or Mtb AM-binding fragment thereof (especially an antibody fragment), as described, e.g., in U.S. Pat. No. 5,739,277. The term "salvage receptor binding epitope" may refer to an epitope of the Fc region of an IgG molecule (e.g., IgG1, IgG2, IgG3, or IgG4) that is responsible for in-creasing the in vivo serum half-life of the IgG molecule (e.g., Ghetie et al., 18 Ann. Rev. Immunol. 739 (2000). Antibodies with substitutions in an Fc region thereof and increased serum half-lives are also described in WO 00/42072, WO 02/060919; Shields et al., 276 J. Biol. Chem. 6591 (2001); Hinton, 279 J. Biol. Chem. 6213-6216 (2004). For example, a nucleic acid molecule encoding the salvage receptor binding epitope can be linked in frame to a nucleic acid encoding a polypeptide sequence described herein so that the fusion protein expressed by the engineered nucleic acid molecule comprises the salvage receptor binding epitope and a polypeptide sequence described herein. In another embodiment, the serum half-life can also be increased, for example, by attaching other polypeptide sequences.

Other types of functional moieties are known in the art and can be readily used in the methods and compositions of the present disclosure based on the teachings contained herein.

In an embodiment, the disclosure provides a method of reducing an activity of Mtb AM in a subject in need thereof, comprising administering to said subject a therapeutically effective amount of the anti-Mtb AM antibody, or Mtb AM-binding fragment thereof, as described herein.

In an embodiment, the disclosure provides a method of treating a *Mycobacterium tuberculosis* infection in a subject, comprising administering to the subject an amount of the anti-Mtb AM antibody, or Mtb AM-binding fragment thereof, as described herein, or the pharmaceutical composition described herein, effective to treat a *Mycobacterium tuberculosis* infection.

In an embodiment, the disclosure provides a method of reducing the likelihood of an *Mycobacterium tuberculosis* infection in a subject, comprising administering to the subject who does not have a *Mycobacterium tuberculosis* infection an amount of the anti-Mtb AM antibody, or Mtb AM-binding fragment thereof, as described herein, or the pharmaceutical composition described herein, effective to reduce the likelihood of an *Mycobacterium tuberculosis* infection.

In an embodiment, the disclosure provides a method of treating a disease, disorder, or condition mediated by, or related to increased activity of *Mycobacterium tuberculosis* in a subject, comprising administering to said subject a therapeutically effective amount of the anti-Mtb AM antibody, or Mtb AM-binding fragment thereof, as described herein, or the pharmaceutical composition described herein.

In an embodiment, an assay device is provided for selectively detecting a one or more bacteria from the MTC group in a biological sample comprising: a first portion comprising a first plurality of anti-Mtb AM antibodies, or Mtb AM-binding fragments thereof, as described herein, or anti-mycobacterial AM-antibodies, wherein the antibodies or fragments are each attached to their own reporting entity; and a second portion comprising a second plurality of anti-Mtb AM antibodies, or Mtb AM-binding fragments thereof, as described herein, or anti-mycobacterial AM-antibodies.

MTC is a genetically related group of *Mycobacterium* species that can cause tuberculosis in humans or other animals and includes *Mycobacterium tuberculosis, M africanum, M. canettii, M. bovis, M. microti, M. orygis, M. caprae, M. pinnipedii, M. suricattae*, and *M. mungi*.

In embodiments, the reporting entity comprises a nanoparticle. In an embodiment the nanoparticle is a gold nanoparticle.

In embodiments, the reporting entity comprises an enzyme.

In embodiments, the second plurality of anti-Mtb AM-antibodies, or Mtb AM-binding fragments thereof, or anti-mycobacterial AM-antibodies, is affixed to a solid support of the device.

In embodiments, the first plurality of anti-Mtb AM-antibodies, or Mtb AM-binding fragments thereof, or anti-mycobacterial AM-antibodies, is not affixed to a solid support of the device.

In embodiments, the solid support comprises nitrocellulose.

In embodiments, the device further comprises a fluid sample pad prior in sequential order to the first and second portions.

In embodiments, the device further comprises a control portion subsequent in sequential order to the first and second portions.

In embodiments, the control portion comprises a third plurality of antibodies, immobilized on a solid support of the device, and which third plurality of antibodies are capable of binding the first plurality of anti-Mtb AM-antibodies, or Mtb AM-binding fragments thereof, or anti-mycobacterial AM-antibodies each attached to their own reporting molecule.

In embodiments, the device further comprises a fluid-absorbent wicking pad subsequent in sequential order to the first and second portions, and third portion if present.

In embodiments, the second plurality of anti-Mtb AM-antibodies, or Mtb AM-binding fragments thereof, as described herein, or anti-mycobacterial AM-antibodies.

In embodiments, the reporting entity is an enzyme which is horseradish peroxidase (HRP) or alkaline phosphatase (AP).

Also provided is a lateral flow assay device for detecting a *Mycobacterium tuberculosis* in a biological sample comprising: a first portion comprising a first plurality of anti-Mtb AM-antibodies, or Mtb AM-binding fragments thereof, as disclosed herein, comprising a heavy chain variable region of SEQ ID NOS: 13 or 14 and a light chain variable region of SEQ ID NO:15; or comprising a heavy chain variable region of SEQ ID NO: 33 and a light chain variable region of SEQ ID NO:17, wherein the antibodies or fragments are each attached to their own reporting entity; and a second portion comprising a second plurality of anti-Mtb AM-antibodies, or Mtb AM-binding fragments thereof, or anti-mycobacterial AM-antibodies.

In some embodiments, the assay device comprises one or more pluralities of anti-Mtb AM antibodies, or Mtb AM-binding fragments thereof, or anti-mycobacterial AM-antibodies, wherein at least one of the pluralities of anti-Mtb AM antibodies, or Mtb AM-binding fragments thereof, or anti-mycobacterial AM-antibodies, comprises a non-human constant region or a modified non-human constant region. In some embodiments, the assay device comprises one or more pluralities of anti-Mtb AM antibodies, or Mtb AM-binding fragments thereof, or anti-mycobacterial AM-antibodies, wherein at least one of the pluralities of anti-Mtb AM antibodies, or Mtb AM-binding fragments thereof, or anti-mycobacterial AM-antibodies, comprises a murine constant region or a modified murine constant region.

In an embodiment, the reporting entity comprises an enzyme.

In an embodiment, the reporting entity comprises a gold nanoparticle, horseradish peroxidase (HRP), or alkaline phosphatase (AP). In an embodiment, the reporting entity comprises a gold nanoparticle.

In an embodiment, the second plurality of anti-Mtb AM antibodies, or Mtb AM-binding fragments thereof, or anti-mycobacterial AM-antibodies is affixed to a solid support of the device.

In an embodiment, the first plurality of anti-Mtb AM antibodies, or Mtb AM-binding fragments thereof, or anti-mycobacterial AM-antibodies is not affixed to a solid support of the device.

In an embodiment, the solid support comprises nitrocellulose.

In an embodiment, the device further comprises a fluid sample pad prior in sequential order to the first and second portions.

In an embodiment, the device further comprises a control portion subsequent in sequential order to the first and second portions.

In an embodiment, the control portion comprises a third plurality of antibodies, immobilized on a solid support of the device, and which third plurality of antibodies are capable of binding the first plurality of anti-Mtb AM antibodies, or Mtb AM-binding fragments thereof, or anti-mycobacterial AM-antibodies, each attached to their own reporting molecule.

In an embodiment, the device further comprises a fluid-absorbent wicking pad subsequent in sequential order to the first and second portions, and third portion if present.

In an embodiment, the second plurality of anti-Mtb AM antibodies, or Mtb AM-binding fragments thereof, comprise anti-Mtb AM antibodies, or Mtb AM-binding fragments thereof as described herein, comprising a heavy chain variable region of SEQ ID NOS: 13 or 14 and a light chain variable region of SEQ ID NO:15; or comprising a heavy chain variable region of SEQ ID NO: 33 and a light chain variable region of SEQ ID NO:17.

In an embodiment, a method is provided for detecting one or more bacteria from the MTC group in a biological sample comprising (a) contacting the device described herein with the sample; and
(b) observing if one or more bacteria from the MTC group bind to the second plurality of anti-Mtb AM antibodies, or Mtb AM-binding fragments thereof, or anti-mycobacterial AM-antibodies,
wherein if such anti-Mtb AM antibodies, or Mtb AM-binding fragments thereof, or anti-mycobacterial AM-antibodies, bind, then one or more bacteria from the MTC group have been detected in the biological sample; and if no anti-Mtb AM antibodies, or Mtb AM-binding fragments thereof, or anti-mycobacterial AM-antibodies, bind to the second plurality of anti-Mtb AM antibodies, or Mtb AM-binding fragments thereof, or anti-mycobacterial AM-antibodies, then bacteria from the MTC group have not been detected in the biological sample.

Many available anti-Mtb AM antibodies react with mycobacterial strains from both the MTC group and non-tuberculous mycobacteria (NTM). Provided herein are antibodies and antigen-binding fragments thereof that bind to MTC, and show significantly decreased or no binding to NTM. Accordingly, provided is a method of discriminating between one or more bacteria from the MTC group and NTM using anti-Mtb AM antibodies, or Mtb AM-binding fragments thereof, or anti-mycobacterial AM-antibodies, including the anti-Mtb AM antibodies, or Mtb AM-binding fragments thereof, disclosed herein. Diagnostic tests based on such methods that are able to discriminate between virulent and non-virulent *Mycobacterium* infections, or one or more bacteria from the MTC group and NTM, represent a major advance that will greatly reduce wasted effort and consequent costs resulting from further diagnostic tests and/or therapeutic procedures.

In one embodiment, provided is a method of detecting and/or distinguishing one or more bacteria from the MTC group and NTM in a biological sample, the method comprising:

(a) providing a biological sample comprising an Mtb antigen;

(b) contacting the sample with a first anti-Mtb AM antibody, or Mtb AM-binding fragment thereof, or anti-mycobacterial AM-antibody, wherein the first anti-Mtb AM antibody, or Mtb AM-binding fragment thereof, or anti-mycobacterial AM-antibody, binds one or more bacteria from the MTC group, but does not substantially bind to NTM;

(c) observing if the Mtb antigen in the biological sample binds to the first anti-Mtb AM antibody, or Mtb AM-binding fragment thereof, or anti-mycobacterial AM-antibody;

(d) contacting the sample with a second anti-Mtb antibody, or Mtb-binding fragment thereof, or anti-mycobacterial AM-antibody, wherein the second anti-Mtb AM antibody, or Mtb AM-binding fragment thereof, or anti-mycobacterial AM-antibody binds to one or more bacteria from the MTC group and to NTM;

(e) observing if the Mtb antigen in the biological sample binds to the second anti-Mtb AM antibody, or Mtb AM-binding fragment thereof, or anti-mycobacterial AM-antibody; wherein if the Mtb antigen in the biological sample binds to the first and the second anti-Mtb AM antibodies, or Mtb AM-binding fragments thereof, or anti-mycobacterial AM-antibody, then one or more bacteria from the MTC group have been detected in the biological sample; and wherein if the Mtb antigen in the biological sample binds to the second, but not the first anti-Mtb AM antibody, or Mtb AM-binding fragment thereof, or anti-mycobacterial AM-antibody, then NTM has been detected in the biological sample.

In embodiments, the method further comprises obtaining the sample from a subject.

In embodiments, the sample is blood, blood plasma, blood serum, cerebrospinal fluid, bile acid, saliva, synovial fluid, pleural fluid, pericardial fluid, peritoneal fluid, feces, nasal fluid, ocular fluid, intracellular fluid, intercellular fluid, lymph fluid, urine, tissue, sputum, bladder washings, oral washings, tissue samples, touch preps, or fine-needle aspirates. The biological sample can be concentrated prior to use.

In embodiments, the subject is human. In some embodiment, the subject is a non-human mammal. In some embodiments, the subject is a cow, buffalo, lion. In some embodiment, the subject is an animal suitable for use in research, including, but not limited to, mouse, rat, rabbit, guinea pig, sheep, goat, and nonhuman primate. In some embodiments, the antibodies and antigen-binding fragments thereof disclosed herein bind to one or more strains of the MTC group, which comprises *Mycobacterium tuberculosis, M. africanum, M. canettii, M. bovis, M. microti, M. orygis, M. caprae, M. pinnipedii, M. suricattae*, and *M. mungi*. In some embodiments, the antibodies and antigen-binding fragments thereof disclosed herein bind to *M. bovis*.

As used herein, the term "antibody" refers to an intact antibody, i.e., with complete Fc and Fv regions. "Fragment" refers to any portion of an antibody, or portions of an antibody linked together, such as, in non-limiting examples, a Fab, F(ab)2, a single-chain Fv (scFv), which is less than the whole antibody but which is an antigen-binding portion and which competes with the intact antibody of which it is a fragment for specific binding. In this case, the antigen is the Mtb capsule AM.

As such a fragment can be prepared, for example, by cleaving an intact antibody or by recombinant means. See generally, Fundamental Immunology, Ch. 7 (Paul, W., ed., 2nd ed. Raven Press, N.Y. (1989), hereby incorporated by reference in its entirety). Antigen-binding fragments may be produced by recombinant DNA techniques or by enzymatic or chemical cleavage of intact antibodies or by molecular biology techniques. In some embodiments, a fragment is an Fab, Fab', F(ab')2, Fd, Fv, complementarity determining region (CDR) fragment, single-chain antibody (scFv), (a variable domain light chain (VL) and a variable domain heavy chain (VH) linked via a peptide linker. In an embodiment, the scFv comprises a variable domain framework sequence having a sequence identical to a human variable domain FR1, FR2, FR3 or FR4. In an embodiment, the scFv comprises a linker peptide from 5 to 30 amino acid residues long. In an embodiment, the scFv comprises a linker peptide comprising one or more of glycine, serine and threonine residues.

In an embodiment the linker of the scFv is 10-25 amino acids in length. In an embodiment the peptide linker comprises glycine, serine and/or threonine residues. For example, see Bird et al., Science, 242: 423-426 (1988) and Huston et al., Proc. Natl. Acad. Sci. USA, 85:5879-5883 (1988), each of which are hereby incorporated by reference in their entirety, or a polypeptide that contains at least a portion of an antibody that is sufficient to confer Mtb capsular AM-specific antigen binding on the polypeptide, including a diabody. From N-terminus to C-terminus, both the mature light and heavy chain variable domains comprise the regions FR1, CDR1, FR2, CDR2, FR3, CDR3 and FR4. The assignment of amino acids to each domain is in accordance with the definitions of Kabat, Sequences of Proteins of Immunological Interest (National Institutes of Health, Bethesda, Md. (1987 and 1991)), Chothia & Lesk, J. Mol. Biol. 196:901-917 (1987), or Chothia et al., Nature 342: 878-883 (1989), each of which are hereby incorporated by reference in their entirety). As used herein, the term "polypeptide" encompasses native or artificial proteins, protein fragments and polypeptide analogs of a protein sequence. A polypeptide may be monomeric or polymeric. As used herein, an Fd fragment means an antibody fragment that consists of the VH and CH1 domains; an Fv fragment consists of the V1 and VH domains of a single arm of an antibody; and a dAb fragment (Ward et al., Nature 341:544-546 (1989) hereby incorporated by reference in its entirety) consists of a VH domain. In some embodiments, fragments are at least 5, 6, 8 or 10 amino acids long. In other embodiments, the fragments are at least 14, at least 20, at least 50, or at least 70, 80, 90, 100, 150 or 200 amino acids long.

The term "monoclonal antibody" as used herein refers to an antibody member of a population of substantially homogeneous antibodies, i.e., the individual antibodies comprising the population are identical except for possible mutations, e.g., naturally occurring mutations, that may be present in minor amounts. Thus, the modifier "monoclonal" indicates the character of the antibody as not being a mixture of discrete antibodies. In certain embodiments, such a monoclonal antibody typically includes an antibody comprising a polypeptide sequence that binds a target an Mtb capsular AM, wherein the target-binding polypeptide sequence was obtained by a process that includes the selection of a single target binding polypeptide sequence from a plurality of polypeptide sequences. For example, the selection process can be the selection of a unique clone from a plurality of clones, such as a pool of hybridoma clones, phage clones, or recombinant DNA clones. In contrast to polyclonal antibody preparations, which typically include different antibodies directed against different determinants (epitopes), each monoclonal antibody of a monoclonal antibody preparation is directed against a single determinant on an antigen. In addition to their specificity, monoclonal antibody preparations are advantageous in that they are typically uncontaminated by other immunoglobulins. Thus an identified monoclonal antibody can be produced by non-hybridoma techniques, e.g., by appropriate recombinant means once the sequence thereof is identified.

In an embodiment of the inventions described herein, the antibody is isolated. As used herein, the term "isolated antibody" refers to an antibody that by virtue of its origin or source of derivation has one, two, three or four of the following: (1) is not associated with naturally associated components that accompany it in its native state, (2) is free of other proteins from the same species, (3) is expressed by a cell from a different species, and (4) does not occur in nature.

As used herein, a "human antibody" unless otherwise indicated is one whose sequences correspond to (i.e., are identical in sequence to) an antibody that could be produced by a human and/or has been made using any of the techniques for making human antibodies as disclosed herein, but not one which has been made in a human. This definition of a human antibody specifically excludes a humanized antibody. A "human antibody" as used herein can be produced using various techniques known in the art, including phage-display libraries (Hoogenboom and Winter, J. Mol. Biol., 227:381 (1991); Marks et al., J. Mol. Biol., 222:581 (1991), hereby incorporated by reference in their entireties, by methods described in Cole et al., Monoclonal Antibodies and Cancer Therapy, Alan R. Liss, p. 77 (1985) hereby incorporated by reference in its entirety; Boerner et al., J. Immunol., 147(1):86-95 (1991) hereby incorporated by reference in its entirety, van Dijk and van de Winkel, Curr. Opin. Pharmacol., 5: 368-74 (2001) hereby incorporated by reference in its entirety, and by administering the antigen (e.g., Mtb capsular AM or an entity comprising such) to a transgenic animal that has been modified to produce such antibodies in response to antigenic challenge, but whose endogenous loci have been disabled, e.g., immunized xeno-mice (see, e.g., U.S. Pat. Nos. 5,939,598; 6,075,181; 6,114,598; 6,150,584 and 6,162,963 to Kucherlapati et al. regarding XENOMOUSE™ technology, each of which patents are hereby incorporated by reference in their entireties), e.g., VelocImmune® (Regeneron, Tarrytown, NY), e.g., UltiMab® platform (Medarex, now Bristol Myers Squibb, Princeton, NJ). See also, for example, Li et al., Proc. Natl. Acad. Sci. USA, 103:3557-3562 (2006) regarding human antibodies generated via a human B-cell hybridoma technology. See also KM Mouse® system, described in PCT Publication WO 02/43478 by Ishida et al., in which the mouse carries a human heavy chain transchromosome and a human light chain transgene, and the TC mouse system, described in Tomizuka et al. (2000) Proc. Natl. Acad. Sci. USA 97:722-727, in which the mouse carries both a human heavy chain transchromosome and a human light chain transchromosome, both of which are hereby incorporated by reference in their entireties. In each of these systems, the transgenes and/or transchromosomes carried by the mice comprise human immunoglobulin variable and constant region sequences.

The term "human antibody", as used herein, is intended to include antibodies having variable regions in which both the framework and CDR regions are sequences of human origin or identical thereto other than antibodies naturally occurring in a human or made in a human. Furthermore, if the antibody (e.g., an intact antibody rather than, for example, an Fab fragment) contains a constant region, the constant region also is derived from such human sequences, e.g., human germline sequences, or mutated versions of human germline sequences. The human antibodies of the invention may include amino acid residues not encoded by human sequences (e.g., mutations introduced by random or site-specific mutagenesis in vitro or by somatic mutation in vivo). However, the term "human antibody", as used herein, is not intended to include antibodies in which CDR sequences derived from the germline of another mammalian species, such as a mouse, have been grafted onto human framework sequences. In one non-limiting embodiment, where the human antibodies are human monoclonal antibodies, such antibodies can be produced by a hybridoma which includes a B cell obtained from a transgenic nonhuman animal, e.g., a transgenic mouse, having a genome comprising a human heavy chain transgene and a light chain transgene fused to an immortalized cell.

In an embodiment, the Mtb capsular AM antibody described herein is a recombinant human antibody. The term "recombinant human antibody", as used herein, includes all human antibodies that are prepared, expressed, created or isolated by recombinant means, such as antibodies isolated from an animal (e.g., a mouse) that is transgenic or transchromosomal for human immunoglobulin genes or a hybridoma prepared therefrom, antibodies isolated from a host cell transformed to express the human antibody, e.g., from a transfectoma, antibodies isolated from a recombinant, combinatorial human antibody library, and antibodies prepared, expressed, created, or isolated by any other means that involve splicing of all or a portion of a human immunoglobulin gene sequences to other DNA sequences. Such recombinant human antibodies have variable regions in which the framework and CDR regions are derived from human germline immunoglobulin sequences. In certain embodiments, however, such recombinant human antibodies can be subjected to in vitro mutagenesis (or, when an animal transgenic for human Ig sequences is used, in vivo somatic mutagenesis) and thus the amino acid sequences of the VH and VL regions of the recombinant antibodies are sequences that, while derived from and related to human germline VH and VL sequences, may not naturally exist within the human antibody germline repertoire in vivo.

"Humanized" forms of non-human (e.g., murine) antibodies are chimeric antibodies that contain minimal sequence derived from non-human immunoglobulin. In one embodiment, a humanized antibody is a human immunoglobulin (recipient antibody) in which residues from a hypervariable region (HVR) of the recipient are replaced by residues from a HVR of a non-human species (donor antibody) such as mouse, rat, rabbit, or nonhuman primate having the desired specificity, affinity, and/or capacity. In some instances, FR residues of the human immunoglobulin variable domain are replaced by corresponding non-human residues. These modifications may be made to further refine antibody performance. Furthermore, in a specific embodiment, humanized antibodies may comprise residues that are not found in the recipient antibody or in the donor antibody. In an embodiment, the humanized antibodies do not comprise residues that are not found in the recipient antibody or in the donor antibody. In general, a humanized antibody will comprise substantially all of at least one, and typically two, variable domains, in which all or substantially all of the hypervariable loops correspond to those of a non-human immunoglobulin, and all or substantially all of the FRs are those of a human immunoglobulin sequence. The humanized antibody optionally will also comprise at least a portion of an immunoglobulin constant region (Fc), typically that of a human immunoglobulin. See, e.g., Jones et al., Nature 321:522-525 (1986); Riechmann et al., Nature 332:323-329 (1988); Presta, Curr. Op. Struct. Biol. 2:593-596 (1992); Vaswani and Hamilton, Ann. Allergy, Asthma & Immunol. 1:105-115 (1998); Harris, Biochem. Soc. Transactions 23:1035-1038 (1995); Hurle and Gross, Curr. Op. Biotech. 5:428-433 (1994); and U.S. Pat. Nos. 6,982,321 and 7,087,409, the contents of each of which references and patents are hereby incorporated by reference in their entirety. In one embodiment where the humanized antibodies do comprise residues that are not found in the recipient antibody or in the donor antibody, the Fc regions of the antibodies are modified as described in WO 99/58572, the content of which is hereby incorporated by reference in their entireties.

Techniques to humanize a monoclonal antibody are described in U.S. Pat. Nos. 4,816,567; 5,807,715; 5,866,692; 6,331,415; 5,530,101; 5,693,761; 5,693,762; 5,585,089; and 6,180,370, the content of each of which is hereby incorporated by reference in its entirety.

A number of "humanized" antibody molecules comprising an antigen-binding site derived from a non-human immunoglobulin have been described, including antibodies having rodent or modified rodent V regions and their associated complementarity determining regions (CDRs) fused to human constant domains. See, for example, Winter et al. Nature 349: 293-299 (1991), Lobuglio et al. Proc. Nat. Acad. Sci. USA 86: 4220-4224 (1989), Shaw et al. J. Immunol. 138: 4534-4538 (1987), and Brown et al. Cancer Res. 47: 3577-3583 (1987), the content of each of which is hereby incorporated by reference in its entirety. Other references describe rodent hypervariable regions or CDRs grafted into a human supporting framework region (FR) prior to fusion with an appropriate human antibody constant domain. See, for example, Riechmann et al. Nature 332: 323-327 (1988), Verhoeyen et al. Science 239: 1534-1536 (1988), and Jones et al. Nature 321: 522-525 (1986), the content of each of which is hereby incorporated by reference in its entirety. Another reference describes rodent CDRs supported by recombinantly veneered rodent framework regions—European Patent Publication No. 0519596 (incorporated by reference in its entirety). These "humanized" molecules are designed to minimize unwanted immunological response toward rodent anti-human antibody molecules which limits the duration and effectiveness of therapeutic applications of those moieties in human recipients. The antibody constant region can be engineered such that it is immunologically inert (e.g., does not trigger complement lysis). See, e.g. PCT Publication No. WO99/58572; UK Patent Application No. 9809951.8. Other methods of humanizing antibodies that may also be utilized are disclosed by Daugherty et al., Nucl. Acids Res. 19: 2471-2476 (1991) and in U.S. Pat. Nos. 6,180,377; 6,054,297; 5,997,867; 5,866,692; 6,210,671; and 6,350,861; and in PCT Publication No. WO 01/27160 (each incorporated by reference in its entirety).

Other forms of humanized antibodies have one or more CDRs (CDR L1, CDR L2, CDR L3, CDR H1, CDR H2, or CDR H3) which are altered with respect to the original antibody, which are also termed one or more CDRs "derived from" one or more CDRs from the original antibody.

In some embodiments, the anti-Mtb AM antibody or Mtb AM-binding fragment thereof has a non-human constant region or a modified non-human constant region. In some embodiments, constant region is from a non-human primate, a mouse, a rat, a sheep, a goat, or a rabbit.

In embodiments, the antibodies or fragments herein can be produced recombinantly, for example antibodies expressed using a recombinant expression vector transfected into a host cell, antibodies isolated from a recombinant, combinatorial human antibody library, antibodies isolated from an animal (e.g., a mouse) that is transgenic for human immunoglobulin genes.

In an embodiment, the Mtb capsular AM antibody described herein is capable of specifically binding or specifically binds an Mtb capsular AM. As used herein, the terms "is capable of specifically binding" or "specifically binds" refers to the property of an antibody or fragment of binding to the specified antigen with a dissociation constant that is <1 □M, preferably <1 nM and most preferably <10 pM. In an embodiment, the Kd of the antibody (or fragment) for Mtb capsular AM is better than 1.0 nM. In an embodiment, the Kd of the antibody (or fragment) for Mtb capsular AM is better than 1.5 nM. In an embodiment, the Kd of the antibody (or fragment) for Mtb capsular AM is 1.8 nM or more. In an embodiment, the Kd of the antibody (or fragment) for avirulent Mtb capsular AM is a lower affinity than its Kd for virulent Mtb capsular AM. An epitope that "specifically binds" to an antibody or a polypeptide is a term well understood in the art. A molecular entity is said to exhibit "specific binding" or "preferential binding" if it reacts or associates more frequently, more rapidly, with greater duration and/or with greater affinity with a particular cell or substance than it does with alternative cells or substances. An antibody "specifically binds" or "preferentially binds" to a target if it binds with greater affinity, avidity, more readily, and/or with greater duration than it binds to other substances. For example, an antibody that specifically or preferentially binds to a Mtb capsular AM conformational epitope is an antibody that binds this epitope with greater affinity, avidity, more readily, and/or with greater duration than it binds to other Mtb capsular AM epitopes or non-Mtb capsular AM epitopes. It is also understood by reading this definition that, for example, an antibody (or moiety or epitope) that specifically or preferentially binds to a first target may or may not specifically or preferentially bind to a second target. As such, "specific binding" or "preferential binding" does not necessarily require, although it can include, exclusive binding.

The term "compete", as used herein with regard to an antibody, means that a first antibody, or an antigen-binding portion thereof, binds to an epitope in a manner sufficiently similar to the binding of a second antibody, or an antigen-binding portion thereof, such that the result of binding of the first antibody with its cognate epitope is detectably decreased in the presence of the second antibody compared to the binding of the first antibody in the absence of the second antibody. The alternative, where the binding of the second antibody to its epitope is also detectably decreased in the presence of the first antibody, can, but need not be the case. That is, a first antibody can inhibit the binding of a second antibody to its epitope without that second antibody inhibiting the binding of the first antibody to its respective epitope. However, where each antibody detectably inhibits the binding of the other antibody with its cognate epitope or ligand, whether to the same, greater, or lesser extent, the antibodies are said to "cross-compete" with each other for binding of their respective epitope(s). Both competing and cross-competing antibodies are encompassed by the present invention. Regardless of the mechanism by which such competition or cross-competition occurs (e.g., steric hindrance, conformational change, or binding to a common epitope, or portion thereof), the skilled artisan would appreciate, based upon the teachings provided herein, that such competing and/or cross-competing antibodies are encompassed and can be useful for the methods disclosed herein.

Depending on the amino acid sequences of the constant domains of their heavy chains, antibodies (immunoglobulins) can be assigned to different classes. The antibody or fragment can be, e.g., any of an IgG, IgD, IgE, IgA or IgM antibody or fragment thereof, respectively. In an embodiment the antibody is an immunoglobulin G. In an embodiment the antibody fragment is a fragment of an immunoglobulin G. In an embodiment the antibody is an IgG1, IgG2, IgG2a, IgG2b, IgG3 or IgG4. In an embodiment the antibody comprises sequences from a human IgG1, human IgG2, human IgG3 or human IgG4. A combination of any of these antibodies subtypes can also be used. One consideration in selecting the type of antibody to be used is the desired serum half-life of the antibody. For example, an IgG generally has a serum half-life of 23 days, IgA 6 days, IgM 5 days, IgD 3 days, and IgE 2 days. (Abbas A K, Lichtman A H, Pober J S. Cellular and Molecular Immunology, 4th edition, W.B. Saunders Co., Philadelphia, 2000, hereby incorporated by reference in its entirety).

The "variable region" or "variable domain" of an antibody refers to the amino-terminal domains of the heavy or light chain of the antibody. The variable domain of the heavy chain may be referred to as "VH." The variable domain of the light chain may be referred to as "VL." These domains are generally the most variable parts of an antibody and contain the antigen-binding sites. The term "variable" refers to the fact that certain portions of the variable domains differ extensively in sequence among antibodies and are used in the binding and specificity of each particular antibody for its particular antigen. However, the variability is not evenly distributed throughout the variable domains of antibodies. It is concentrated in three segments called hypervariable regions (HVRs) both in the light chain and the heavy chain variable domains. The more highly conserved portions of variable domains are called the framework regions (FR).

The variable domains of native heavy and light chains each comprise four FR regions, largely adopting a beta-sheet configuration, connected by three HVRs, which form loops connecting, and in some cases forming part of, the beta-sheet structure. The HVRs in each chain are held together in close proximity by the FR regions and, with the HVRs from the other chain, contribute to the formation of the antigen-binding site of antibodies (see Kabat et al., Sequences of Proteins of Immunological Interest, Fifth Edition, National Institute of Health, Bethesda, Md. (1991)). The constant domains are not involved directly in the binding of an antibody to an antigen, but exhibit various effector functions, such as participation of the antibody in antibody-dependent cellular toxicity.

The "light chains" of antibodies (immunoglobulins) from any vertebrate species can be assigned to one of two clearly distinct types, called kappa (D) and lambda (D), based on the amino acid sequences of their constant domains.

"Framework" or "FR" residues are those variable domain residues other than the HVR residues as herein defined.

The term "hypervariable region" or "HVR" when used herein refers to the regions of an antibody variable domain which are hypervariable in sequence and/or form structurally defined loops. Generally, antibodies comprise six HVRs; three in the VH (H1, H2, H3) and three in the VL (L1, L2, L3). In native antibodies, H3 and L3 display the most diversity of the six HVRs, and H3 in particular is believed to play a unique role in conferring fine specificity to antibodies. See, e.g., Xu et al., Immunity 13:37-45 (2000); Johnson and Wu, in Methods in Molecular Biology 248:1-25 (Lo, ed., Human Press, Totowa, N.J., 2003). Indeed, naturally occurring camelid antibodies consisting of a heavy chain only are functional and stable in the absence of light chain. See, e.g., Hamers-Casterman et al., Nature 363:446-448 (1993); Sheriff et al., Nature Struct. Biol. 3:733-736 (1996). A number of HVR delineations are in use and are encompassed herein. The Kabat Complementarity Determining Regions (CDRs) are based on sequence variability and are the most commonly used (Kabat et al., Sequences of Proteins of Immunological Interest, 5th Ed. Public Health Service, National Institutes of Health, Bethesda, Md. (1991) hereby incorporated by reference in its entirety). Chothia refers instead to the location of the structural loops (Chothia and Lesk, J. Mol. Biol. 196:901-917 (1987)). The AbM HVRs represent a compromise between the Kabat HVRs and Chothia structural loops, and are used by Oxford Molecular's AbM antibody modeling software. The "contact" HVRs are based on an analysis of the available complex crystal structures. HVRs may comprise "extended HVRs" as follows: 24-36 or 24-34 (L1), 46-56 or 50-56 (L2) and 89-97 or 89-96 (L3) in the VL and 26-35 (H1), 50-65 or 49-65 (H2) and 93-102, 94-102, or 95-102 (H3) in the VH. The variable domain residues are numbered according to Kabat et al., supra, for each of these definitions.

The term "Fc region" herein is used to define a C-terminal region of an immunoglobulin heavy chain, including native sequence Fc regions and variant Fc regions. Although the boundaries of the Fc region of an immunoglobulin heavy chain might vary, the human IgG heavy chain Fc region is usually defined to stretch from an amino acid residue at position Cys226, or from Pro230, to the carboxyl-terminus thereof. The C-terminal lysine of the Fc region may be removed, for example, during production or purification of the antibody, or by recombinantly engineering the nucleic acid encoding a heavy chain of the antibody. Accordingly, an intact antibody as used herein may be an antibody with or without the otherwise C-terminal lysine.

Compositions or pharmaceutical compositions comprising the antibodies, ScFvs or fragments of antibodies disclosed herein preferably comprise stabilizers to prevent loss of activity or structural integrity of the protein due to the effects of denaturation, oxidation, or aggregation over a period of time during storage and transportation prior to use. The compositions or pharmaceutical compositions can comprise one or more of any combination of salts, surfactants, pH and tonicity agents such as sugars that contribute to overcoming aggregation problems. Where a composition or pharmaceutical composition of the present invention is used as an injection, it is desirable to have a pH value in an approximately neutral pH range. It is also advantageous to minimize surfactant levels to avoid bubbles in the formulation which are detrimental for injection into subjects. In an embodiment, the composition or pharmaceutical composition is in liquid form and stably supports high concentrations of bioactive antibody in solution and is suitable for inhalational or parenteral administration. In an embodiment, the composition or pharmaceutical composition is suitable for intravenous, intramuscular, intraperitoneal, intradermal and/or subcutaneous injection. In an embodiment, the composition or pharmaceutical composition is in liquid form and has minimized risk of bubble formation and anaphylactoid side effects. In an embodiment, the composition or pharmaceutical composition is isotonic. In an embodiment, the composition or pharmaceutical composition has a pH or 6.8 to 7.4.

In an embodiment the ScFvs or fragments of antibodies disclosed herein are lyophilized and/or freeze dried and are reconstituted for use.

The antibodies, or fragments of antibodies, or compositions, or pharmaceutical compositions described herein can also be lyophilized or provided in any suitable forms including, but not limited to, injectable solutions or inhalable solutions, gel forms, and tablet forms.

The term "Kd", as used herein, is intended to refer to the dissociation constant of an antibody-antigen interaction. One way of determining the Kd or binding affinity of antibodies to Mtb capsular AM is by measuring binding affinity Using a Dip and Read assay using an immobilized antigen and monoclonal antibodies (Octet Red96 ForteBio, Fremont, CA). (The affinity constant is the inverted dissociation constant). Biotinylated Mtb capsular AM can be diluted into PBS+0.1% BSA, 0.02% Tween20 and 0.05% sodium azide (Kinetics Buffer, ForteBio) and dipped in to wells containing serial diluted mAbs starting from 37.75 nM. The concentrations of the Fab proteins are determined by ELISA and/or SDS-PAGE electrophoresis using a IgG1 standard monoclonal antibody of known concentration as a standard. Kinetic association rates (kon) and dissociation rates (koff) are obtained simultaneously by fitting the data to a 1:1 Langmuir binding model (Karlsson, R. Roos, H. Fagerstam, L. Petersson, B. (1994). Methods Enzymology 6. 99-110, the content of which is hereby incorporated in its entirety) using the BIA evaluation program. Equilibrium dissociation constant (Kd) values are calculated as koff/kon. This protocol is suitable for use in determining binding affinity of an antibody or fragment to any Mtb capsular AM. Other protocols known in the art may also be used. For example, ELISA of Mtb capsular AM with mAb can be used to determine the kD values.

The term "Fc domain" herein is used to define a C-terminal region of an immunoglobulin heavy chain, including native sequence Fc regions and variant Fc regions. Although the boundaries of the Fc domain of an immunoglobulin heavy chain might vary, the human IgG heavy chain Fc domain is usually defined to stretch from an amino acid residue at position Cys226, or from Pro230, to the carboxyl-terminus thereof. The C-terminal lysine of the Fc domain may be removed, for example, by recombinantly engineering the nucleic acid encoding it.

In embodiments, the antibody comprises an Fc domain. In an embodiment, the Fc domain has the same sequence or 99% or greater sequence similarity with a human IgG1 Fc domain. In an embodiment, the Fc domain has the same sequence or 99% or greater sequence similarity with a human IgG2 Fc domain. In an embodiment, the Fc domain has the same sequence or 99% or greater sequence similarity with a human IgG3 Fc domain. In an embodiment, the Fc domain has the same sequence or 99% or greater sequence similarity with a human IgG4 Fc domain. In an embodiment, the Fc domain is not mutated. In an embodiment, the Fc domain is mutated at the CH2-CH3 domain interface to increase the affinity of IgG for FcRn at acidic but not neutral pH. In an embodiment, the Fc domain has the same sequence as a human IgG1 Fc domain.

The invention encompasses modifications to the variable regions disclosed herein. For example, the invention includes antibodies comprising functionally equivalent variable regions and CDRs which do not significantly affect their properties as well as variants which have enhanced or decreased activity and/or affinity. For example, the amino acid sequence may be mutated to obtain an antibody with the desired binding affinity to Mtb AM. Modification of polypeptides is routine practice in the art and need not be described in detail herein. Examples of modified polypeptides include polypeptides with conservative substitutions of amino acid residues, one or more deletions or additions of amino acids which do not significantly deleteriously change the functional activity, or which mature (enhance) the affinity of the polypeptide for its ligand, or use of chemical analogs.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue or the antibody fused to an epitope tag. Other insertional variants of the antibody molecule include the fusion to the N- or C-terminus of the antibody of an enzyme or a polypeptide which increases the half-life of the antibody in the blood circulation.

Substitution variants have at least one amino acid residue in the antibody molecule removed and a different residue inserted in its place. The sites of greatest interest for substitutional mutagenesis include the hypervariable regions, but framework alterations are also contemplated. Conservative substitutions are shown in Table 1 under the heading of "conservative substitutions." If such substitutions result in a change in biological activity, then more substantial changes, denominated "exemplary substitutions" in Table 1, or as further described below in reference to amino acid classes, may be introduced and the products screened.

TABLE 1

Amino Acid Substitutions

| Original Residue | Conservative Substitutions | Exemplary Substitutions |
|---|---|---|
| Ala (A) | Val | Val; Leu; Ile |
| Arg (R) | Lys | Lys; Gln; Asn |
| Asn (N) | Gln | Gln; His; Asp, Lys; Arg |
| Asp (D) | Glu | Glu; Asn |
| Cys (C) | Ser | Ser; Ala |
| Gln (Q) | Asn | Asn; Glu |
| Glu (E) | Asp | Asp; Gln |
| Gly (G) | Ala | Ala |
| His (H) | Arg | Asn; Gln; Lys; Arg |
| Ile (I) | Leu | Leu; Val; Met; Ala; Phe; Norleucine |
| Leu (L) | Ile | Norleucine; Ile; Val; Met; Ala; Phe |
| Lys (K) | Arg | Arg; Gln; Asn |
| Met (M) | Leu | Leu; Phe; Ile |
| Phe (F) | Tyr | Leu; Val; Ile; Ala; Tyr |
| Pro (P) | Ala | Ala |
| Ser (S) | Thr | Thr |
| Thr (T) | Ser | Ser |
| Trp (W) | Tyr | Tyr; Phe |
| Tyr (Y) | Phe | Trp; Phe; Thr; Ser |
| Val (V) | Leu | Ile; Leu; Met; Phe; Ala; Norleucine |

Substantial modifications in the biological properties of the antibody are accomplished by selecting substitutions that differ significantly in their effect on maintaining (a) the structure of the polypeptide backbone in the area of the substitution, for example, as a Q-sheet or helical conformation, (b) the charge or hydrophobicity of the molecule at the target site, or (c) the bulk of the side chain. Naturally occurring residues are divided into groups based on common side-chain properties:

(1) Non-polar: Norleucine, Met, Ala, Val, Leu, le;
(2) Polar without charge: Cys, Ser, Thr, Asn, Gin;
(3) Acidic (negatively charged): Asp, Glu;
(4) Basic (positively charged): Lys, Arg;
(5) Residues that influence chain orientation: Gly, Pro; and
(6) Aromatic: Trp, Tyr, Phe, His.

Non-conservative substitutions are made by exchanging a member of one of these classes for another class.

One type of substitution, for example, that may be made is to change one or more cysteines in the antibody, which may be chemically reactive, to another residue, such as, without limitation, alanine or serine. For example, there can be a substitution of a non-canonical cysteine. The substitution can be made in a CDR or framework region of a variable domain or in the constant region of an antibody. In some embodiments, the cysteine is canonical. Any cysteine residue not involved in maintaining the proper conformation of the antibody also may be substituted, generally with serine, to improve the oxidative stability of the molecule and prevent aberrant cross-linking. Conversely, cysteine bond(s) may be added to the antibody to improve its stability, particularly where the antibody is an antibody fragment such as an Fv fragment.

The antibodies may also be modified, e.g., in the variable domains of the heavy and/or light chains, e.g., to alter a binding property of the antibody. Changes in the variable region can alter binding affinity and/or specificity. In some embodiments, no more than one to five conservative amino acid substitutions are made within a CDR domain. In other embodiments, no more than one to three conservative amino acid substitutions are made within a CDR domain. For example, a mutation may be made in one or more of the CDR regions to increase or decrease the $K_D$ of the antibody for Mtb AM, to increase or decrease koff, or to alter the binding specificity of the antibody. Techniques in site-directed mutagenesis are well-known in the art.

A modification or mutation may also be made in a framework region or constant region to increase the half-life of an anti-Mtb AM antibody. See, e.g., PCT Publication No. WO 00/09560. A mutation in a framework region or constant region can also be made to alter the immunogenicity of the antibody, to provide a site for covalent or non-covalent binding to another molecule, or to alter such properties as complement fixation, FcR binding and antibody-dependent cell-mediated cytotoxicity. In embodiments, a single antibody may have mutations in any one or more of the CDRs or framework regions of the variable domain or in the constant region.

In an embodiment, an antibody described herein is recombinantly produced. In an embodiment, the fusion protein is produced in a eukaryotic expression system.

In an embodiment, the fusion protein produced in the eukaryotic expression system comprises glycosylation at a residue on the Fc portion corresponding to Asn297.

In an embodiment, the disclosure provides a composition comprising an antibody, or antigen-binding fragment thereof, as described herein. In an embodiment, the composition is a pharmaceutical composition. In an embodiment the composition or pharmaceutical composition comprising the antibody, or antigen-binding fragment thereof, described herein is substantially pure with regard to the antibody, or antigen-binding fragment thereof. A composition or pharmaceutical composition comprising the antibody, or antigen-binding fragment thereof, described herein is "substantially pure" with regard to the antibody or fragment when at least 60% to 75% of a sample of the composition or pharmaceutical composition exhibits a single species of the antibody, or antigen-binding fragment thereof. A substantially pure composition or pharmaceutical composition comprising the antibody, or antigen-binding fragment thereof, described herein can comprise, in the portion thereof which is the antibody, or antigen-binding fragment, 60%, 70%, 80% or 90% of the antibody, or antigen-binding fragment, of the single species, more usually about 95%, and preferably over 99%. Purity or homogeneity may be tested by a number of means well known in the art, such as polyacrylamide gel electrophoresis or HPLC.

In embodiments, the antibody, or antigen-binding fragment thereof, binds to a linear epitope. In embodiments, the antibody, or antigen-binding fragment thereof, binds to a linear oligosaccharide epitope.

In an embodiment, "determining" as used herein means experimentally determining.

"And/or" as used herein, for example, with option A and/or option B, encompasses the separate embodiments of (i) option A, (ii) option B, and (iii) option A plus option B.

All combinations of the various elements described herein are within the scope of the invention unless otherwise indicated herein or otherwise clearly contradicted by context.

All references cited herein are incorporated herein in their entireties.

The following non-limiting example serves to further illustrate embodiments of the invention.

Example

Individuals at different stages of Mtb infection and exposure were recruited and their sera screened for AM reactivity by ELISA. The individuals were living in the US (mostly immigrants from TB endemic regions) and categorized by the results of their Tuberculin skin-tests (TST) and Interferon Gamma Release Assays (IGRA), or TB diagnostic test results. PPD+ individuals were TST-positive (TST+), had a history of BCG vaccination and were IGRA-negative (IGRA−); latent (controlled) Mtb infection (LTBI) were TST+ and IGRA+; and subjects diagnosed with active TB had symptomatic microbiologically confirmed disease. PPD-volunteers were TST-negative and their sera were used as a baseline control.

It was observed that AM serum titers correlated with protective functions against Mtb such as enhanced Mtb opsonophagocytosis and intracellular growth restriction in vitro (FIGS. 1A-E and FIGS. 2A-D). Human serum IgG titers to AM and the lipidated cell wall antigen lipoarabinomanan (LAM) were significantly correlated with protective effects such as enhanced Mtb opsonophagocytosis and intracellular growth restriction by human macrophages in vitro. These protective effects were associated with antibody reactivity to certain AM oligosaccharides using a glycan microarray (FIGS. 1A-E and FIG. 2A-D). This indicates that the Mtb capsule exposes different polysaccharide epitopes and some could be more pertinent than others. Passive transfer of polyclonal AM IgG from a few subjects showed significant reduction in the bacterial burden in the lungs of mice infected with a low dose of Mtb resembling human infection (25 CFU; FIG. 2D).

Subjects with high AM IgG titer in their sera were identified. High titer subjects (ELISA OD405 >1.0) were depleted of AM-specific IgG by incubating the serum with magnetic beads conjugated to biotinylated AM. Recombinant human mAbs were generated from isolated single memory B cells. Single memory B cell sorting was performed for AM (isolated from the virulent Mtb strain H37Rv) with PBMCs from a high anti-AM IgG titer Tuberculin skin test (TST)+ healthy individual with polyclonal anti-AM Ab functions against Mtb. Immunoglobulin genes were cloned, sequenced and re-expressed in 293T HEK cells.

Antibody AM009 (also known as T1AM09 as per Chen et al., J Clin Invest. 2020 Apr. 1; 130(4):1808-1822) was generated from the memory B cells obtained from a PPD+ individual with high AM serum titers (subject V57), and whose serum demonstrated protective functions against Mtb. This subject's sera restricted Mtb growth intracellularly in vitro by a THP-1 (monocyte cell line) based growth inhibition assay and reduced the bacterial burden in the lungs of mice infected with Mtb in vivo (FIGS. 2A-D). The binding of AM009 (also known as T1AM09) to AM was characterized and the mAb's functions in vitro investigated (FIGS. 3A-E). It was determined that some of the regions of the heavy or light chain are essential for OS-binding and activity. Mutants with substitutions in the complementarity determining regions (CDRs) and framework regions (FRs) were designed and expressed (FIGS. 4A-C).

AM009 (also known as T1AM09) was not remarkably somatically mutated, and shared sequence similarity in both heavy (91%) and light chains (89%) at the nucleotide level. The AM009 (also known as T1AM09) antibody sequence also contained features that were consistent with polysaccharide specific antibodies such as multiple repeating hydrophobic residues and a moderately long CDRH3 (14 amino acids long). The heavy chain is derived from the VH1-2*02 germline gene (QVQLVQSGAEVKKPGASVKVSCKASGYTFTGYYMHWVRQAPGQGLEWM

GWINPNSGGTNYAQKFQGRVTMTRDTSISTAYMELSRLRSDDTAVYYCA

R (SEQ ID NO: 43)).

The light chain was IGKV1-39 derived (SEQ ID NO: 44)
(DIQMTQSPSSLSASVGDRVTITCRASQSISSYLNWYQQKPGKAPKLLI

YAASSLQSGVPSRFSGSGSGTDFTLTISSLQPEDFATYYCQQSYSTE I

K.

Notably, there is an overrepresentation of polysaccharide specific antibodies from the VH3 family reported.

BioLayer Interferometry (BLI) was used to measure the affinity of the mAb to AM. The binding specificity of mAbs to different Mtb strains (whole bacteria as well as capsular AM and cell wall LAM) was determined by immunofluorescence and ELISA.

Figure 6A:
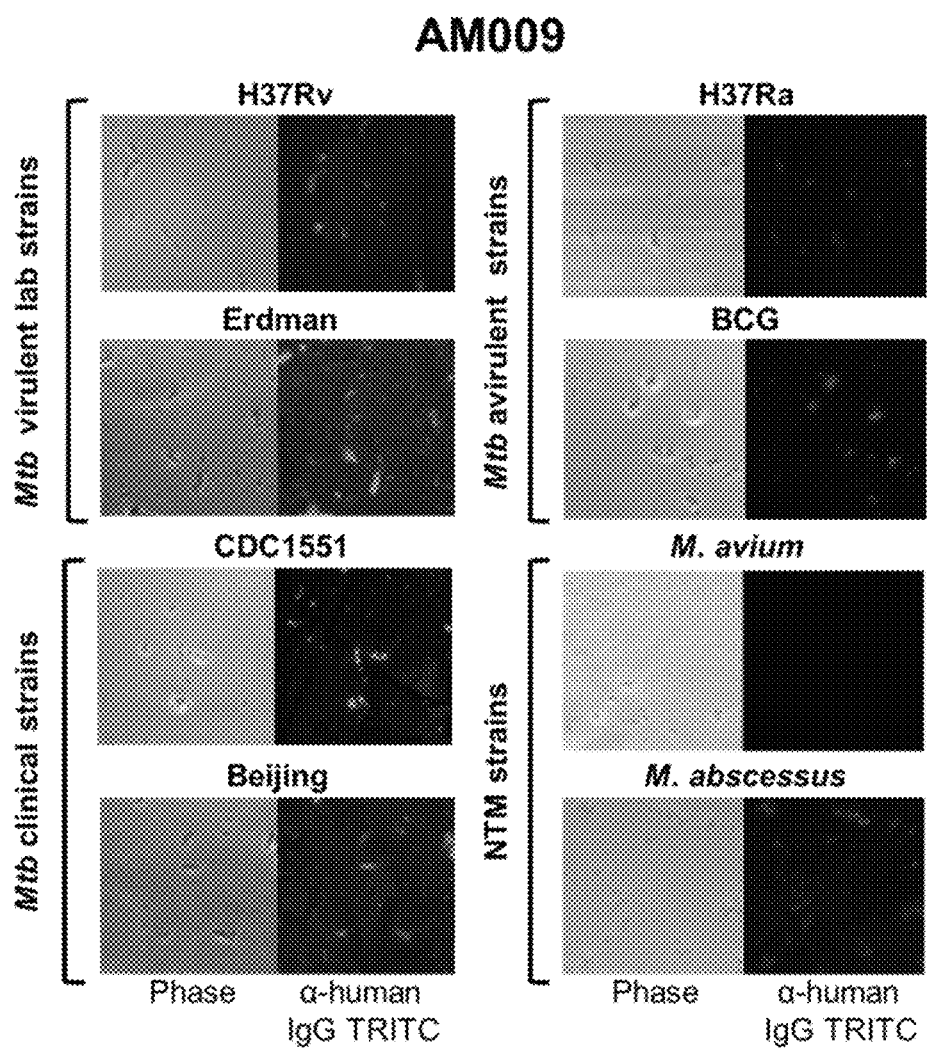
FIGS. 6A and 6B illustrate the specific binding of anti-Mtb AM antibody AM009 (also known as T1AM09) to mycobacterial strains by immunofluorescence. Mycobacteria were grown without detergent to preserve the capsule.
Figure 6B:
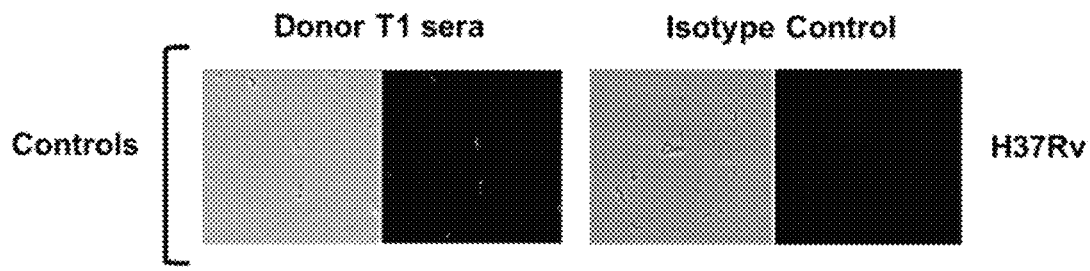

To further characterize the polysaccharide epitopes, mAbs were tested for their binding reactivity to 30 synthesized AM oligosaccharide fragments. Thirty oligosaccharide fragments representing the components of AM were designed and synthesized by Dr. Todd Lowary's group (University of Alberta, Canada). In binding characterization, AM009 (also known as T1AM09) binds with very high affinity to AM by BLI (KD=5.12×10$^{-8}$ M) and binds to the whole bacteria with an intact capsule. This is an exceptionally high affinity for a polysaccharide mAb. In addition, AM009 (also known as T1AM09) binds a novel polysaccharide epitope which could be specific for capsular AM (FIGS. 5A and B). AM009 (also known as T1AM09) has increased specificity for the virulent Mtb H37Rv AM (but less for the avirulent H37Ra AM) isolated from the capsule with some degree of cross-reactivity with H37Rv LAM (FIGS. 3A-E). Similarly, immunofluorescence experiments demonstrated that anti-Mtb AM antibody AM009 (also known as T1AM09) showed increased specificity for virulent laboratory (H37Rv and Erdman) and clinical strains (CDC1551 and Beijing) of Mtb, as compared to avirulent strains of the Mtb complex group (H37Ra and BCG Pasteur) and non-tuberculosis mycobacteria (*M. avium* and *M. abscessus*) (FIGS. 6A and 6B). Accordingly, anti-Mtb AM antibodies, and Mtb AM-binding fragments thereof, disclosed herein are useful to discriminate between MTC strains and non-tuberculosis mycobacteria.

Figure 7A:
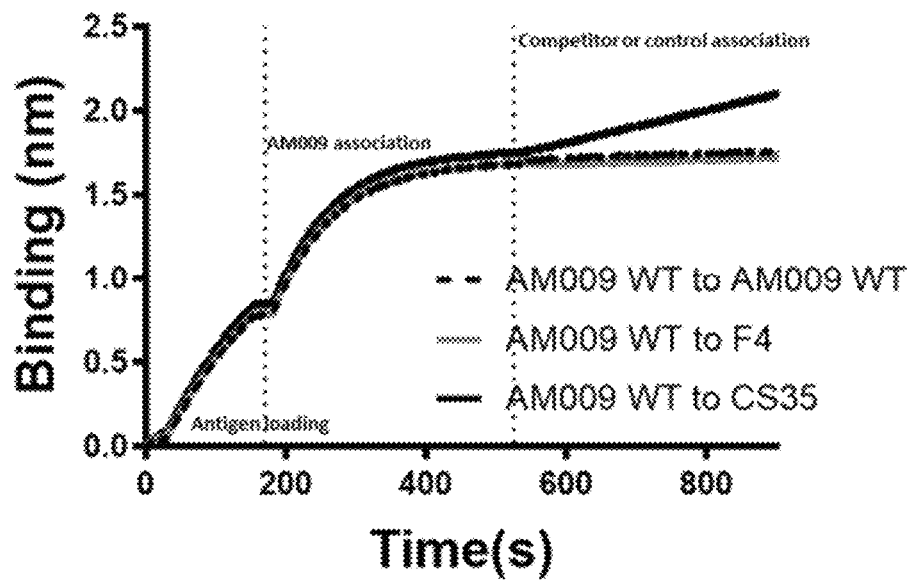
FIGS. 7A and 7B illustrate that anti-Mtb AM antibodies AM009 (also known as T1AM09) and AM009 G100bA do not compete with murine anti-LAM mAb CS-35. Shown are two-phase binding experiment detecting AM009 (FIG. 7A) and AM009 G100bA (FIG. 7B) competition with CS-35 compared self- and negative-controls. Negative control: isotype matched mAb F4 to a flavivirus.
Figure 7B:
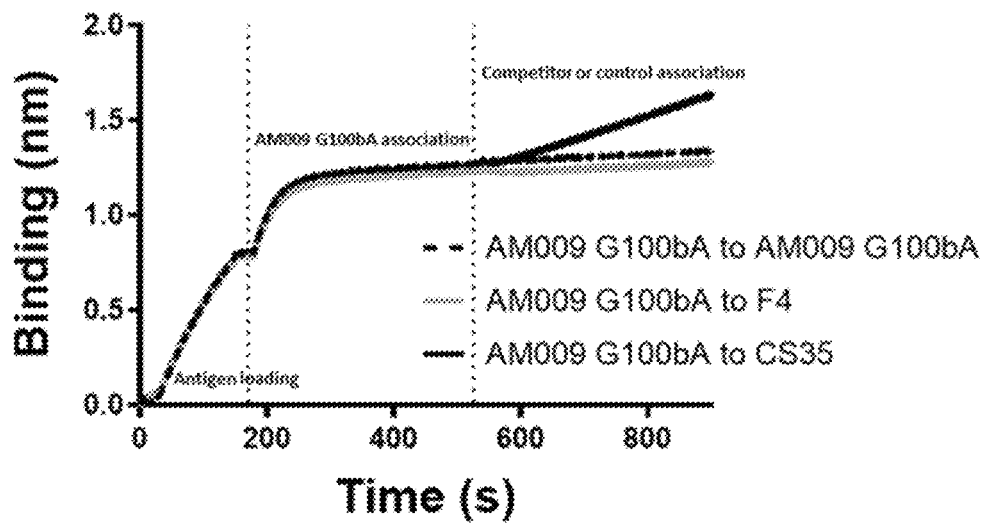

Murine mAb CS-35 to LAM was used as a positive control for high affinity binding to LAM and AM isolated from various mycobacteria strains. The epitope for CS-35 is very well defined and the mAb binds a conserved terminal arabinofuranose epitope on LAM and AM from several strains of mycobacteria. Preliminary data suggest that both AM009 (also known as T1AM09) and CS-35 bind the fixed Mtb with the capsule, but recognize different epitopes. In cross-competition ELISA, CS-35 and AM009 (also known as T1AM09) do not compete—when CS-35 was used as a competitor mAb, AM009 (also known as T1AM09) binding to AM remained unchanged. Similarly, two-phase binding experiments showed that anti-Mtb AM antibodies AM009 (also known as T1AM09) and G100bA do not compete with widely used murine mAb to LAM (CS-35) and thus can be used in combination with CS-35 and many other anti-LAM mAbs for urinary LAM diagnostics (FIGS. 7 and B).

Moreover, AM009 (also known as T1AM09) had very distinct reactivity to certain AM OS. AM009 (also known as T1AM09) has high affinity for compounds 18-19 and 21-22. Murine mAb to LAM, CS-35 was the positive control. Most other murine mAbs that bind AM and LAM compete with CS-35, but AM009 (also known as T1AM09) exhibits preferential binding to epitopes that are different than CS-35, suggesting that the epitope specificities of antibodies in humans and mice recognized different Mtb capsular AM epitopes.

Human mAbs targeting polysaccharides from the Mtb capsule can restrict Mtb growth using in vitro cell-based assays and in vivo using humanized FcγR mice. In preliminary studies, AM009 (also known as T1AM09) and one of the mutants enhanced Mtb opsonophagocytosis in human macrophages in vitro. These data indicate that AM009 (also known as T1AM09) has functions consistent with the functions observed in the serum (FIGS. 2A-D). Collectively, the data indicate that AM0009 (also known as T1AM09) is unique and has exceptionally high binding specificity for virulent Mtb.

Figure 8A:
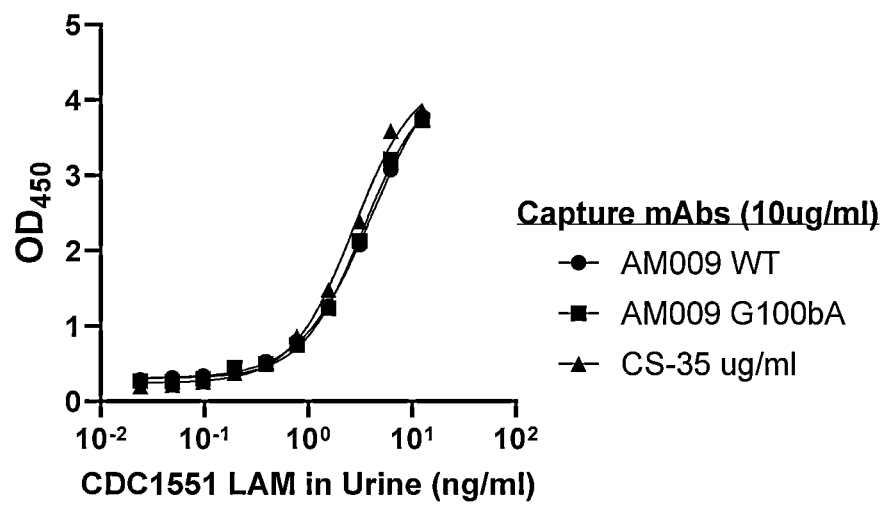
FIGS. 8A and 8B illustrate that high affinity human mAbs directed to distinct AM epitopes can capture and detect low levels of LAM in urine.
Figure 8B:
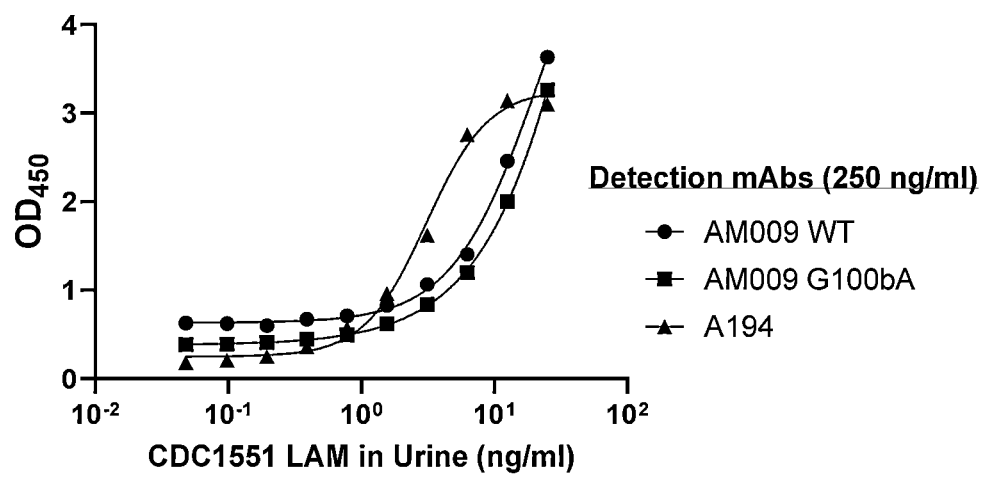
Figure 9A:
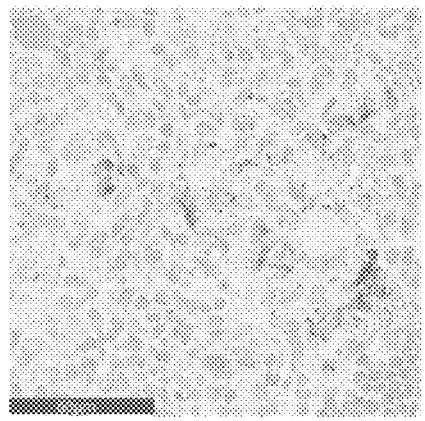
FIGS. 9A, 9B, 9C, 9D, 9E, and 9F illustrates that anti Mtb antibody AM009 (also known as T1AM09) detects extra- and intracellular Mtb and LAM in lung tissues of Mtb-infected mice. Histology and immunohistochemistry of Mtb infected murine lung (scale bar 60 μm) showing intra- and extracellular staining of Mtb CDC1551 by (FIG. 9A) AM009 and (FIG. 9B) Acid-Fast Bacilli (AFB); and intra- and extracellular staining of Mtb CDC1551 by (FIG. 9C) AM009, and (FIG. 9D) lack of positive AFB outside inflammatory regions. (arrows indicate LAM within macrophages). Overall lack of staining of non-infected murine tissue (scale bar 500 μm) by AM009 (FIG. 9E).
Figure 9B:
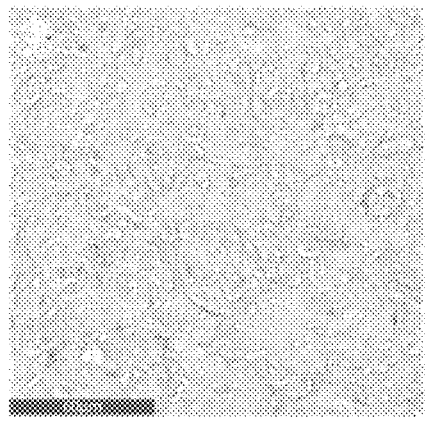
Figure 9C:
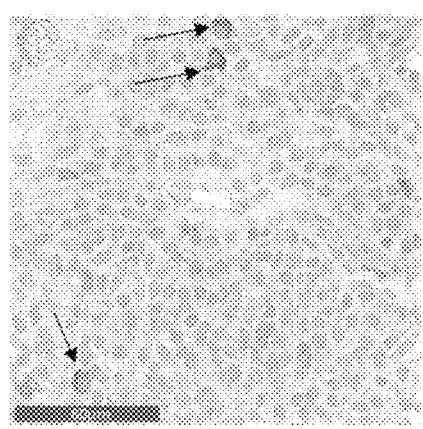
Figure 9D:
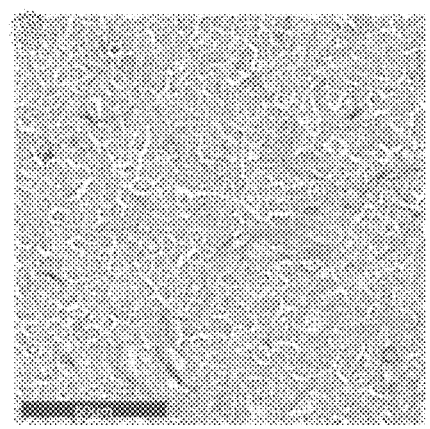
Figure 9E:
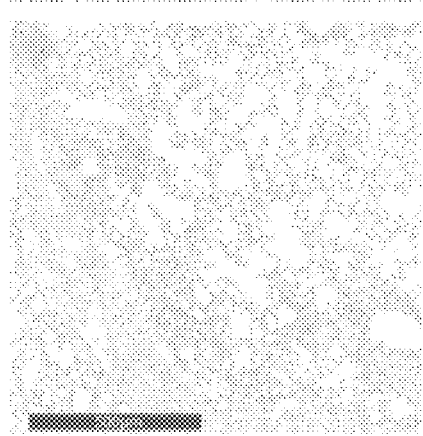
Figure 9F:
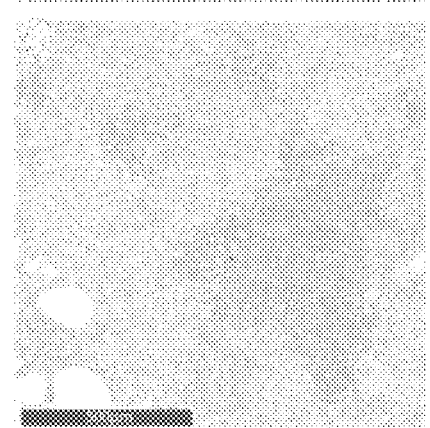

Further, it was shown that high affinity anti-Mtb AM antibodies AM009 (also known as T1AM09) and AM009 G100bA can capture and detect low levels of LAM in urine. As illustrated in FIGS. 8A and B, anti-Mtb AM antibodies AM009 (also known as T1AM09) and G100bA are comparable capture mAbs to the widely used murine mAb to LAM (CS-35). In addition, AM009 (also known as T1AM09) and G100bA can be used as detection mAbs in combination with CS-35 to detect LAM diluted in urine.

Finally, it was shown that anti-Mtb AM antibody AM009 (also known as T1AM09) has increased sensitivity for intra- and extracellular Mtb and LAM in infected tissue compared to Acid Fast Bacilli staining (Ziehl Neelsen) with no off-target effects in unaffected tissue (FIG. 9).

AM009-1 Heavy Chain Variable Region (Amino Acid Sequence) (AM009 is Also Known as T1AM09)

```
                                          (SEQ ID NO: 13)
QVQLVESGAE VKKPGASVKV SCKASGYTFS TYWIHWMRQA

PGQGPEWMGW IIPKSGGTNY AQKFQGRVAM TRDTSLNTVY

MELSRLTSDD TAVYYCARGI LLNGIGAFDY WGQGTLVTVS S
```

AM009-1 Heavy Chain Variable Region (Nucleotide Sequence) (AM009 is Also Known as T1AM09)

```
                                          (SEQ ID NO: 34)
CAGGTGCAGCTGGTGGAGTCTGGGGCTGAGGTGAAGAAGCCTGGGGCCT

CAGTGAAGGTCTCCTGCAAGGCTTCTGGGTACACCTTCTCCACCTACTG

GATCCACTGGATGCGGCAGGCCCCTGGACAAGGGCCTGAGTGGATGGGG

TGGATCATCCCTAAGAGTGGCGGCACAAACTATGCACAGAAGTTTCAGG

GCAGGGTCGCCATGACCAGGGACACGTCCCTCAATACAGTCTACATGGA

GTTGAGCAGGCTGACATCGGACGACACGGCCGTTTATTATTGTGCGAGA

GGTATTCTGTTGAACGGAATTGGGGCCTTTGACTACTGGGGCCAGGGAA

CCCTGGTCACCGTCTCCTCA
```

AM009-2 Heavy Chain Variable Region (Amino Acid Sequence) (AM009 is Also Known as T1AM09)

```
                                          (SEQ ID NO: 14)
QVQLVESGAE VKKPGASVKV SCKASGYTFA TYWIHWMRQA

PGQGPEWMGW IIPKSGGTNY AQKFQGRVAM TRDTSLNTVY

MELSRLTSDD TAVYYCARGI LLNGIGAFDY WGQGTLVTVS S
```

AM009-2 Heavy Chain Variable Region (Nucleotide Sequence) (AM009 is Also Known as T1AM09)

```
                                          (SEQ ID NO: 35)
CAGGTGCAGCTGGTGGAGTCTGGGGCTGAGGTGAAGAAGCCTGGGGCCT

CAGTGAAGGTCTCCTGCAAGGCTTCTGGGTACACCTTCGCCACCTACTG

GATCCACTGGATGCGGCAGGCCCCTGGACAAGGGCCTGAGTGGATGGGG

TGGATCATCCCTAAGAGTGGCGGCACAAACTATGCACAGAAGTTTCAGG

GCAGGGTCGCCATGACCAGGGACACGTCCCTCAATACAGTCTACATGGA

GTTGAGCAGGCTGACATCGGACGACACGGCCGTTTATTATTGTGCGAGA

GGTATTCTGTTGAACGGAATTGGGGCCTTTGACTACTGGGGCCAGGGAA

CCCTGGTCACCGTCTCCTCA
```

AM009 Kappa Chain Variable Region (Amino Acid Sequence) (AM009 is Also Known as T1AM09)

```
DIVMTQSPSS LSASVGDRVT ITCRTSQTVS SNLNWYQQRP

GKAPKLLISG ISDLHSGVPS RFSGSGSGTD FTLTISSLQP

EDSATYYCQQ SYSLPRTFGQ GTKVEIK SEQ ID NO: 15)
```

AM009 Kappa Chain Variable Region (Nucleotide Sequence) (AM009 is Also Known as T1AM09)

```
                                          (SEQ ID NO: 36)
GATATTGTGATGACCCAGTCTCCATCCTCCCTGTCCGCATCTGTTGGAG

ACAGAGTCACCATCACTTGCCGGACGAGTCAGACCGTTTCCAGTAATTT

AAATTGGTATCAGCAGAGACCAGGGAAAGCCCCTAAACTCCTGATCTCT

GGTATATCCGATCTGCATAGTGGGGTCCCATCCAGGTTCAGTGGCAGTG

GGTCTGGGACAGATTTCACTCTCACCATCAGCAGTCTGCAGCCTGAAGA

TTCTGCAACTTACTACTGTCAACAGAGTTACAGTCTCCCTCGGACGTTC

GGCCAAGGGACCAAGGTGGAAATCAAA
```

AM009 Heavy Chain—Kabat Numbering (AM009 is Also Known as T1AM09)
CDRH1
TYWIH
(SEQ ID NO:1)
CDRH2
WIIPKSGGTNYAQKFQG
(SEQ ID NO:2)
CDRH3
GILLNGIGAFDY
(SEQ ID NO:3)
AM009 Kappa Chain—Kabat Numbering (AM009 is Also Known as T1AM09)
CDRL1
RTSQTVSSNLN (SEQ ID NO:4)
CDRL2
GISDLHS
(SEQ ID NO:5)
CDRL3
QQSYSLPRT
(SEQ ID NO:6)
AM009-1 Heavy Chain—IMGT Numbering (AM009 is Also Known as T1AM09)
CDRH1
GYTFSTYW
(SEQ ID NO:21, where sequence is GYTFXTYW and X=S)
CDRH2
IIPKSGGT
(SEQ ID NO:22)
CDRH3
ARGILLNGIGAFDY
(SEQ ID NO:23)
AM009-2 Heavy Chain—IMGT Numbering (AM009 is Also Known as T1AM09)
CDRH1
GYTFATYW
(SEQ ID NO:21, where sequence is GYTFXTYW and X=A)
CDRH2
IIPKSGGT
(SEQ ID NO:22)
CDRH3
ARGILLNGIGAFDY
(SEQ ID NO:23)
AM009 Kappa Chain—IMGT Numbering (AM009 is Also Known as T1AM09)
CDRL1
QTVSSN
(SEQ ID NO:24)
CDRL2
GIS
CDRL3
QQSYSLPRT
(SEQ ID NO:25)
Additional Mutants
mutated CDRH3
SRGILLNGIGAFDY
(SEQ ID NO:32)
mutated CDRH3
ARGILLNGIAAFDY
(SEQ ID NO:31)
AM016—Heavy Chain Variable Region (Nucleotide Sequence)

```
                                            (SEQ ID NO: 33)
QVQLVESGAE VKKPGASVKV SCKASGFTFT DYYIHWVRQA

PGQGLEWIGW INPHSGDTNS AQKFQGRVTM TRDTSISTAY

MELSRLRSYD TAVYYCSRDH YYDTSAYNPS DFWGQGTLVT VSS
```

AM016—Heavy Chain Variable Region (Nucleotide Sequence)

```
                                            (SEQ ID NO: 37)
CAGGTACAGCTGGTGGAGTCTGGGGCTGAGGTGAAGAAGCCTGGGGCCT

CAGTGAAGGTCTCCTGCAAGGCTTCTGGATTCACCTTCACCGACTACTA

TATACACTGGGTGCGACAGGCCCCTGGACAAGGGCTTGAGTGGATTGGA

TGGATCAACCCTCACAGTGGTGACACAAACTCTGCACAGAAGTTTCAGG

GCAGGGTCACCATGACCAGGGACACGTCCATCAGCACAGCCTACATGGA

GCTGAGCAGGCTGAGATCTTACGACACGGCCGTCTATTACTGTTCGAGA

GATCACTACTATGATACTAGTGCTTATAACCCCAGTGACTTCTGGGGCC

AGGGAACCCTGGTCACCGTCTCCTCA
```

AM016 Kappa Chain (Amino Acid Sequence)

```
                                            (SEQ ID NO: 17)
EIVLTQSPAT LSLSPGERAT LSCRTSQSVS SNLAWYQQKA

GQTPRLIIYD ASNRATGTPA RFSGSGSGTD FTLTISSLEP

EDFAVYYCQQ RTHWPPFTFG GGTKVEIK
```

AM016 Kappa Chain (Nucleotide Sequence)

```
                                            (SEQ ID NO: 38)
GAAATTGTGTTGACGCAGTCTCCAGCCACCCTGTCTTTGTCTCCAGGGG

AAAGAGCCACCCTCTCCTGTAGGACCAGTCAGAGTGTTAGCAGCAACTT

AGCCTGGTACCAGCAGAAAGCTGGCCAGACTCCCAGGCTCATCATCTAT

GATGCATCCAACAGGGCCACTGGCACCCCAGCCAGGTTCAGTGGCAGTG

GGTCTGGGACAGACTTCACTCTCACCATCAGCAGCCTAGAGCCTGAAGA

TTTTGCGGTTTATTACTGTCAGCAGCGTACCCACTGGCCTCCGTTCACT

TTCGGCGGAGGGACCAAGGTGGAAATCAAA
```

AM016 Heavy Chain—Kabat Numbering
CDRH1
DYYIH
(SEQ ID NO:7)
CDRH2
WINPHSGDTNSAQKFQG
(SEQ ID NO:8)
CDRH3
DHYYDTSAYNPSDF
(SEQ ID NO:9)
AM016 Kappa Chain—Kabat Numbering
CDRL1
RTSQSVSSNLA
(SEQ ID NO:10)
CDRL2
DASNRAT
(SEQ ID NO:11)
CDRL3
QQRTHWPPFT
(SEQ ID NO:12)
AM016 Heavy Chain—IMGT Numbering
CDRH1
GFTFTDYY
(SEQ ID NO:26)
CDRH2
INPHSGDT
(SEQ ID NO:27)
CDRH3
SRDHYYDTSAYNPSDF
(SEQ ID NO:28)
AM016 Kappa Chain—Imgt Numbering
CDRL1
QSVSSN (SEQ ID NO:29)
CDRL2
DAS
CDRL3
QQRTHWPPFT
(SEQ ID NO:30)

AM016 Mutant Heavy Chain Variable Region (Amino Acid Sequence)

(SEQ ID NO: 16)
QVQLVESGAE VKKPGASVKV SCKASGFTFT DYYIHWVRQA

PGQGLEWIGW INPHSGDTNS AQKFQGRVTM TRDTSISTAY

MELSRLRSYD TAVYYCARGI LLNGIGAFDY WGQGTLVTVS S

AM016 Mutant Heavy Chain Variable Region (Nucleotide Sequence)

(SEQ ID NO: 39)
CAGGTACAGCTGGTGGAGTCTGGGGCTGAGGTGAAGAAGCCTGGGGCCT

CAGTGAAGGTCTCCTGCAAGGCTTCTGGATTCACCTTCACCGACTACTA

TATACACTGGGTGCGACAGGCCCCTGGACAAGGGCTTGAGTGGATTGGA

TGGATCAACCCTCACAGTGGTGACACAAACTCTGCACAGAAGTTTCAGG

GCAGGGTCACCATGACCAGGGACACGTCCATCAGCACAGCCTACATGGA

GCTGAGCAGGCTGAGATCTTACGACACGGCCGTCTATTACTGTGCGAGA

GGTATTCTGTTGAACGGAATTGGGGCCTTTGACTACTGGGGCCAGGGAA

CCCTGGTCACCGTCTCCTCAGC

AM016 Mutant A93S Heavy Chain Variable Region (Amino Acid Sequence)

(SEQ ID NO: 18)
QVQLVESGAE VKKPGASVKV SCKASGFTFT DYYIHWVRQA

PGQGLEWIGW INPHSGDTNS AQKFQGRVTM TRDTSISTAY

MELSRLRSYD TAVYYCSRGI LLNGIGAFDY WGQGTLVTVS S

AM016 Mutant A93S Heavy Chain Variable Region (Nucleotide Sequence)

(SEQ ID NO: 40)
CAGGTACAGCTGGTGGAGTCTGGGGCTGAGGTGAAGAAGCCTGGGGCCT

CAGTGAAGGTCTCCTGCAAGGCTTCTGGATTCACCTTCACCGACTACTA

TATACACTGGGTGCGACAGGCCCCTGGACAAGGGCTTGAGTGGATTGGA

TGGATCAACCCTCACAGTGGTGACACAAACTCTGCACAGAAGTTTCAGG

GCAGGGTCACCATGACCAGGGACACGTCCATCAGCACAGCCTACATGGA

GCTGAGCAGGCTGAGATCTTACGACACGGCCGTCTATTACTGTTCGAGA

GGTATTCTGTTGAACGGAATTGGGGCCTTTGACTACTGGGGCCAGGGAA

CCCTGGTCACCGTCTCCTCAGC

AM009_1_G100bA Heavy Chain Variable Region (Amino Acid Sequence)

(SEQ ID NO: 19)
QVQLVESGAE VKKPGASVKV SCKASGYTFS TYWIHWMRQA

PGQGPEWMGW IIPKSGGTNY AQKFQGRVAM TRDTSLNTVY

MELSRLTSDD TAVYYCARGI LLNGIAAFDY WGQGTLVTVS S

AM009_1_G100bA Heavy Chain Variable Region (Nucleotide Sequence)

(SEQ ID NO: 41)
CAGGTGCAGCTGGTGGAGTCTGGGGCTGAGGTGAAGAAGCCTGGGGCCT

CAGTGAAGGTCTCCTGCAAGGCTTCTGGGTACACCTTCTCCACCTACTG

GATCCACTGGATGCGGCAGGCCCCTGGACAAGGGCCTGAGTGGATGGGG

TGGATCATCCCTAAGAGTGGCGGCACAAACTATGCACAGAAGTTTCAGG

GCAGGGTCGCCATGACCAGGGACACGTCCCTCAATACAGTCTACATGGA

GTTGAGCAGGCTGACATCGGACGACACGGCCGTTTATTATTGTGCGAGA

GGTATTCTGTTGAACGGAATTGCGGCCTTTGACTACTGGGGCCAGGGAA

CCCTGGTCACCGTCTCCTCA

AM009_2_G100bA Heavy Chain Variable Region (Amino Acid Sequence)

(SEQ ID NO: 20)
QVQLVESGAE VKKPGASVKV SCKASGYTFA TYWIHWMRQA

PGQGPEWMGW IIPKSGGTNY AQKFQGRVAM TRDTSLNTVY

MELSRLTSDD TAVYYCARGI LLNGIAAFDY WGQGTLVTVS S

AM009_2_G100bA Heavy Chain Variable Region (Nucleotide Sequence)

(SEQ ID NO: 42)
CAGGTGCAGCTGGTGGAGTCTGGGGCTGAGGTGAAGAAGCCTGGGGCCT

CAGTGAAGGTCTCCTGCAAGGCTTCTGGGTACACCTTCGCCACCTACTG

GATCCACTGGATGCGGCAGGCCCCTGGACAAGGGCCTGAGTGGATGGGG

TGGATCATCCCTAAGAGTGGCGGCACAAACTATGCACAGAAGTTTCAGG

GCAGGGTCGCCATGACCAGGGACACGTCCCTCAATACAGTCTACATGGA

GTTGAGCAGGCTGACATCGGACGACACGGCCGTTTATTATTGTGCGAGA

GGTATTCTGTTGAACGGAATTGCGGCCTTTGACTACTGGGGCCAGGGAA

CCCTGGTCACCGTCTCCTCA

---

What is claimed is:

1. An assay device for selectively detecting *Mycobacterium tuberculosis* (Mtb) bacteria or Mtb arabinomannan (AM) in a biological sample, wherein the assay device is a lateral flow assay device or an Enzyme Linked Immunosorbent Assay (ELISA), the assay device comprising:
   (a) a first portion comprising a first plurality of anti-Mtb AM antibodies, or Mtb AM-binding fragments thereof, wherein each anti-Mtb AM antibody, or Mtb AM-binding fragment thereof, comprises a heavy chain variable region and a light chain variable region, wherein each of the heavy chain and the light chain variable regions comprises a CDR1, CDR2, and CDR3; and wherein:
      (i) the sequence of CDR1 of the heavy chain comprises SEQ ID NO: 1; the sequence of CDR2 of the heavy chain comprises SEQ ID NO:2; the sequence of CDR3 of the heavy chain comprises SEQ ID NO:3; the sequence of CDR1 of the light chain comprises SEQ ID NO:4; the sequence of CDR2 of the light chain comprises SEQ ID NO:5; and the sequence of CDR3 of the light chain comprises SEQ ID NO:6; or
      (ii) the sequence of CDR1 of the heavy chain comprises SEQ ID NO: 1; the sequence of CDR2 of the heavy chain comprises SEQ ID NO:2; the sequence of CDR3 of the heavy chain comprises SEQ ID NO:45; the sequence of CDR1 of the light chain comprises SEQ ID NO:4; the sequence of CDR2 of the light chain comprises SEQ ID NO:5; and the sequence of CDR3 of the light chain comprises SEQ ID NO:6, wherein the anti-Mtb antibodies, or Mtb AM-binding fragments thereof, are each attached to their own reporting entity; and
   (b) a second portion comprising a second plurality of anti-Mtb AM antibodies, or Mtb AM-binding fragments thereof.

2. The assay device of claim 1, wherein:
   (a) the heavy chain variable region comprises SEQ ID NO:13 and the light chain variable region comprises SEQ ID NO:15;
   (b) the heavy chain variable region comprises SEQ ID NO:14 and the light chain variable region comprises SEQ ID NO:15;
   (c) the heavy chain variable region comprises SEQ ID NO:19 and the light chain variable region comprises SEQ ID NO:15; or
   (d) the heavy chain variable region comprises SEQ ID NO:20 and the light chain variable region comprises SEQ ID NO:15.

3. The assay device of claim 1, wherein the assay device is a lateral flow assay device.

4. The assay device of claim 3, wherein the reporting entity comprises a gold nanoparticle or an enzyme.

5. The assay device of claim 4, wherein the enzyme is horseradish peroxidase (HRP) or alkaline phosphatase (AP).

6. The assay device of claim 3, further comprising a fluid sample pad prior in sequential order to the first and second portions.

7. The assay device of claim 3, further comprising a control portion subsequent in sequential order to the first and second portions.

8. The assay device of claim 7, further comprising a fluid-absorbent wicking pad subsequent in sequential order to the first and second portions.

9. The assay device of claim 7, wherein the control portion comprises a third plurality of antibodies, immobilized on a solid support, and which third plurality of antibodies are capable of binding the first plurality of anti-Mtb AM antibodies, or Mtb AM-binding fragments thereof.

10. The assay device of claim 1, wherein the second plurality of anti-Mtb AM antibodies, or Mtb AM-binding fragments thereof, is affixed to a solid support.

11. The assay device of claim 10, wherein the solid support comprises nitrocellulose.

12. A method of detecting Mtb bacteria or Mtb AM in a biological sample comprising:
   (a) contacting the assay device of claim 10 the sample; and
   (b) detecting binding of Mtb bacteria or Mtb AM to the first and the second plurality of anti-Mtb AM antibodies.

13. The method of claim 12, wherein the sample is urine or blood.

14. The method of claim 12, wherein:
   (a) the heavy chain variable region comprises SEQ ID NO:13 and the light chain variable region comprises SEQ ID NO:15;
   (b) the heavy chain variable region comprises SEQ ID NO:14 and the light chain variable region comprises SEQ ID NO:15;
   (c) the heavy chain variable region comprises SEQ ID NO:19 and the light chain variable region comprises SEQ ID NO:15; or
   (d) the heavy chain variable region comprises SEQ ID NO:20 and the light chain variable region comprises SEQ ID NO:15.

15. The method of claim 12, wherein the assay device is a lateral flow assay device.

16. The method of claim 15, the assay device further comprises a control portion subsequent in sequential order to the first and second portions.

17. The method of claim 16, wherein the control portion comprises a third plurality of antibodies, immobilized on a solid support, and which third plurality of antibodies are capable of binding the first plurality of anti-Mtb AM antibodies, or Mtb AM-binding fragments.

18. The method of claim 12, wherein the reporting entity comprises a gold nanoparticle or an enzyme.

19. The method of claim 18, wherein the enzyme is HRP or AP.

\* \* \* \* \*